US008975437B2

(12) United States Patent
Kotsianis et al.

(10) Patent No.: US 8,975,437 B2
(45) Date of Patent: *Mar. 10, 2015

(54) PROCESS FOR THE CONTINUOUS TRANSVINYLATION OF CARBOXYLIC ACIDS WITH VINYL ACETATE

(75) Inventors: Ilias S. Kotsianis, Houston, TX (US); Barbara F. M. Kimmich, Bernardsville, NJ (US); Melchior A. Meilchen, Houston, TX (US); Hang Wang, Houston, TX (US); Prashant P. Barve, Baner (IN); Bhaskar D. Kulkarni, Pune (IN); Gopal M. Chaphekar, Pune (IN); Ravindra W. Shinde, Pune (IN); Milind Y. Gupte, Pune (IN); Sanjay P. Kamble, Pune (IN); Satish N. Shintre, Pune (IN)

(73) Assignee: Celanese International Corporation, Dallas, TX (US)

( * ) Notice: Subject to any disclaimer, the term of this patent is extended or adjusted under 35 U.S.C. 154(b) by 651 days.

This patent is subject to a terminal disclaimer.

(21) Appl. No.: 13/068,130

(22) Filed: May 3, 2011

(65) Prior Publication Data

US 2011/0275853 A1     Nov. 10, 2011

Related U.S. Application Data

(60) Provisional application No. 61/343,811, filed on May 4, 2010, provisional application No. 61/343,812, filed on May 4, 2010.

(51) Int. Cl.
| | | |
|---|---|---|
| *C07C 67/02* | (2006.01) | |
| *C07C 53/00* | (2006.01) | |
| *C07C 51/36* | (2006.01) | |
| *C07C 67/10* | (2006.01) | |
| *C07C 51/44* | (2006.01) | |
| *C07C 51/48* | (2006.01) | |

(52) U.S. Cl.
CPC .............. *C07C 67/10* (2013.01); *C07C 51/36* (2013.01); *C07C 51/44* (2013.01); *C07C 51/48* (2013.01)
USPC ........................................ 560/234; 562/606

(58) Field of Classification Search
USPC .......................................... 562/606; 560/234
See application file for complete search history.

(56) References Cited

U.S. PATENT DOCUMENTS

| | | | | |
|---|---|---|---|---|
| 2,245,131 | A | 6/1941 | Hermann et al. | 260/476 |
| 2,997,494 | A | 8/1961 | Brown | 260/410.9 |
| 2,997,495 | A * | 8/1961 | Rutledge et al. | 554/165 |
| 3,000,918 | A | 9/1961 | Wilip et al. | 260/410.9 |
| 3,188,319 | A | 6/1965 | Smidt et al. | 260/326 |
| 3,337,611 | A | 8/1967 | Bearden, Jr. et al. | 260/491 |
| 3,755,387 | A | 8/1973 | Young | 260/410.9 N |
| 4,425,277 | A | 1/1984 | Kawamoto et al. | 260/410.9 N |
| 4,981,973 | A | 1/1991 | Murray | 548/229 |
| 5,155,253 | A | 10/1992 | Murray | 560/225 |
| 5,210,207 | A | 5/1993 | Mokhtarzadeh et al. | 548/239 |
| 5,214,172 | A | 5/1993 | Waller | 554/165 |
| 5,223,621 | A * | 6/1993 | Vallejos et al. | 554/165 |
| 5,342,979 | A | 8/1994 | Mueller et al. | 554/206 |
| 5,741,925 | A | 4/1998 | Mao et al. | 560/116 |
| 6,891,052 | B1 | 5/2005 | Tanner et al. | 554/161 |
| 2011/0275852 | A1 | 11/2011 | Kotsianis et al. | 560/234 |

FOREIGN PATENT DOCUMENTS

| | | | | |
|---|---|---|---|---|
| EP | 1 220 542 | 1/1971 | ............ | C07C 51/42 |
| EP | 1 486 443 | 9/1977 | | |
| EP | 0 376 075 | 7/1990 | ............ | C07C 67/10 |
| EP | 0497340 | * 1/1992 | ............ | C07C 67/10 |
| EP | 0 494 016 | 7/1992 | ............ | C07C 69/01 |
| EP | 0 497 340 | 8/1992 | ............ | C07C 67/10 |
| EP | 0 648 734 | 4/1995 | ............ | C07C 67/055 |
| JP | 06-009492 | 1/1994 | ............ | C07C 69/24 |
| JP | 07-138203 | 5/1995 | ............ | C07C 69/24 |
| JP | 11-171837 | 6/1999 | ............ | C07C 69/767 |
| JP | 2002-322125 | 11/2002 | ............ | C09C 67/10 |
| JP | 2002-322126 | 11/2002 | ............ | C07C 67/10 |

OTHER PUBLICATIONS

Nakagawa et al. "Synthesis of enol and vinyl esters catalyzed by an iridium complex," Tetrahedron Letters, 44, 103-106 (2003).*
Ketterling, et al., "Carboxylic acid transvinylation as catalysed by complexes of palladium acetate with phenanthroline-like ligands," Applied Catalysis, 66, 123-132, 1990.*
Armarego, WLF Perrin, DD., Purification of Laboratory Chemicals (4th Edition). Elsevier, p. 1, 1996.*
Slinckx et al., entitled "The Mechanism of Vinyl Interchange by Nuclear Magnetic Resonance Spectroscopy", Tetrahedron, vol. 22, Issue 9 (1966), pp. 3163-3171.
Slinckx et al., entitled "Kinetics of the Vinyl Interchange Reaction Between Benzoic Acid and vinyl Acetate", Tetrahedron, 23 (1967), pp. 1395-1403.
McKeon, et al., entitled "The Palladium (II) Catalyzed Vinyl Interchange Reaction -I", Tetrahedron, vol. 28, pp. 227-232, 1972, Part I.
McKeon, et al., entitled "The Palladium (II) Catalyzed Vinyl Interchange Reaction-", Tetrahedron, vol. 28, pp. 233-238, 1972, Part II.

(Continued)

*Primary Examiner* — Paul A Zucker
*Assistant Examiner* — Mark Luderer
(74) *Attorney, Agent, or Firm* — Michael W. Ferrell; Ferrells, PLLC; Anna L. Kinney

(57) ABSTRACT

A continuous process is provided for selective formation of a vinyl ester by reactive distillation from a corresponding carboxylic acid. Carboxylic acid, vinyl acetate, and a palladium acetate—bidentate ligand catalyst complex are provided and reacted in a typical embodiment. Acetic acid and vinyl acetate are continuously removed from the reaction mixture and vinyl acetate is recycled to the reaction mixture. The vinyl ester product is separated from the vinyl acetate, residual carboxylic acid, residual acetic acid, and catalyst.

19 Claims, 3 Drawing Sheets

(56) References Cited

OTHER PUBLICATIONS

Ketterling et al., entitled "Carboxylic Acid Transvinylation as Catalysed by Complexes of Palladium Acetate with Phenanthroline-Like Ligands", Applied Catalysis, 66 (1990) pp. 123-132.

Waller, entitled "Transvinylation Catalysts for the Production of Higher Vinylic Esters of Vinyl Acetate", Catalysis of Organic Reactions, Chemical Industries (Dekker) 1994, 53, pp. 397-410.

Rashidi-Ranjbar et al., entitled "Synthesis of Aroamtic Vinyl Esters by Exchange Reaction Catalyzed with Pd(II)", Molecules, May 1, 1999 (Iranian Paper), pp. 135-138.

Murray & Lincoln, entitled "New Catalytic Route to Vinyl Esters", Catalysis Today, 13 (1992) pp. 93-102.

Schultz et al., entitled "The Chemistry of Palladium Complexes VI. Studes on the Palladium(II)-Catalyzed Decomposition of Vinyl Acetate", Journal of Catalysis, 16 (1970) pp. 133-147.

Nakagawa, et al. entitled "Synthesis of Enol and vinyl Esters Catalyzed by an Iridium Complex", Tetrahedron Letters, 44 (2003) pp. 103-106.

T.A. Stephenson, (Mrs.) S.M. Morehouse, A.R.Powell, J.P. Heifer, and Wilkinson, entitled "Carboxylates of Palladium, Platinum, and Rhodium, and Their Adducts", J.C.S., pp. 3632-3640 (1965).

International Search Report and Written Opinion.

* cited by examiner

CONTINUOUS TRANS-VINYLATION PROCESS

PROCESS FOR THE CONTINUOUS TRANSVINYLATION OF CARBOXYLIC ACIDS WITH VINYL ACETATE

CLAIM FOR PRIORITY

This application is based on U.S. Provisional Patent Application No. 61/343,811, entitled Process for the Semi-continuous Transvinylation of Carboxylic Acids with Vinyl Acetate, and U.S. Provisional Patent Application No. 61/343,812, entitled Process for the Continuous Transvinylation of Carboxylic Acids with Vinyl Acetate, filed May 4, 2010, the priorities of both which are hereby claimed and the disclosures of which are incorporated herein by reference.

FIELD OF INVENTION

This invention relates to the continuous transvinylation of carboxylic acids with vinyl acetate to vinyl esters by way of homogeneous catalysis.

BACKGROUND OF THE INVENTION

The reaction of carboxylic acids with vinyl acetate monomer (VAM or VA) to make vinyl esters is well known in the literature. The earliest art teaches transvinylation using a mercury catalyst. See U.S. Pat. No. 2,997,494 to Brown, U.S. Pat. No. 3,000,918 to Wilip, et al., and U.S. Pat. No. 3,337,611 to Bearden, Jr., as well as Slinckx et al., Tetrahedron, Volume 22, Issue 9 (1966) Pages 3163-3171 and Slinckx et al., *Tetrahedron,* 23 (1967) 1395-1403. U.S. Pat. No. 2,245,131 to Herrmann et al. teaches vinyl acetate and benzoic acid transvinylated using a mercury/sulfuric acid catalyst under reflux, and then the volatiles were removed by distillation prior to distillation to recover vinyl benzoate. British Patent No. GB 1486443 to Imperial Chemical describes a transvinylation reaction for the production of a vinyl ester of an organic carboxylic acid by transvinylating a vinyl ester of an organic carboxylic acid with an organic carboxylic acid whose vinyl ester has a lower boiling point than the vinyl ester reactant. Mercury salts are no longer in use due to the toxic nature of mercury-based compounds.

The literature suggests that the preferred catalysts for transvinylation reactions have been mercury- and palladium-based compounds. Transesterification is disclosed by McKeon, et al., Tetrahedron, Vol. 28, p. 227, 1972, Part I. McKeon, et al. show the vinyl interchange reaction between a vinyl ether and an alcohol using a palladium catalyst in a liquid phase batch process. Nitrogen ligands are used to stabilize the catalyst (pyridine). See also McKeon, et al., Tetrahedron, Vol. 28, p. 233, 1972, Part II in which a catalyst precursor is disclosed of either palladium acetate phenyl or palladium acetate biphenyl complexed with monodentate ligands for stability. However, the resulting catalyst was ineffective. Two catalysts prepared were diacetato (2,2'-bipyridyl)palladium(II) and diacetato (1,10-phenanthroline)palladium(II). Vinyl laurate was prepared from lauric acid and vinyl acetate using the palladium acetate complex with 2,2'-bipyridyl. Schultz et al., Journal of Catalysis, 16 (1970) 133-147, discuss the catalyzed decomposition of vinyl acetate into acetic acid and acetaldehyde using a palladium(II)-chloride catalyst. Palladium catalysts are more specifically applied to transvinylation as described in U.S. Pat. No. 3,188,319 to Smidt et al., U.S. Pat. No. 3,755,387 to Young, and U.S. Pat. No. 4,425,277 to Kawamoto et al., as well as Ketterling et al., Applied Catalysis, 66 (1990) 123-132, Waller, Chemical Industries (Dekker) 1994, 53 (Catalysis of Organic Reactions), p 397, Molecules, May 1, 1999 (Iranian Paper), European Patent No. EP376075, and Japanese Patent Nos. JP1994-9492A to Mitsubishi Rayon Co. Ltd., JP1995-138203 to Fuso Chemical Co. Ltd., and JP1999-171837 to Nippon Steel Chemical Co., Ltd. U.S. Pat. No. 3,188,319 to Smidt et al. further discloses use of platinum and rhodium catalysts for less effective transvinylation of various carboxylic acids in a liquid phase with no solvent after forming from a metal chloride or acetate precursor. Ketterling et al. disclose palladium acetate diimine complexes, such as palladium acetate complexes with 2,2'-bipyridine, as catalysts for transvinylation of unsaturated and saturated carboxylic acids. Sabel et al., Chem. Ber. 102, 2939-2950, 1969, describe Pt(II) and Rh(III) used to catalyze a transvinylation reaction. U.S. Pat. No. 4,425,277 to Kawamoto et al. discusses a method for the preparation of alkenyl esters of carboxylic acids, such as benzoic acid, using the combination of a catalyst, such as palladium acetate, and a redox agent. Transvinylation to produce a carboxylic vinyl ester is also taught in Japanese Patent Nos. JP2002-322125 and JP2002-322126 to Japan Vam & Poval Co., Ltd., which describe combining the reactants, palladium acetate catalyst and lithium acetate co-catalyst together and reacting the mixture at 65° C.

Use of ruthenium catalysts in transvinylation is also known in the art. See U.S. Pat. No. 5,155,253 to Murray, as well as Murray & Lincoln, Catalysis Today, 13 (1992) 93-102, which provides a summary of previous patents and Chem Systems Vinyl Neodecanoate (90S8), February 1992, which provides a review of ruthenium transvinylation as well as addressing palladium catalyzed transvinylation. U.S. Pat. No. 4,981,973 to Murray discloses that ruthenium compositions are useful transvinylation catalysts for numerous Bronsted acids and derivatives of Bronsted acids. However, the Murray processes require a carbon monoxide atmosphere, which requires careful handling.

Iridium catalysis, with a NaOAc additive, of liquid phase batch transvinylation of benzoic and other acids with a substituted alkyne is described by Nakagawa, et al. in Tetrahedron Letters 44 (2003) 103-106. The iridium catalyst is formed from a $[Ir(cod)Cl]_2$ precursor.

U.S. Pat. No. 5,210,207 to Mokhtarzadeh, et al. teaches continuous transvinylation by reactive distillation. Mokhtarzadeh, et al. discloses a process for the preparation of numerous vinyl derivatives of Bronsted acids formed by the transvinylation reaction of a vinyl derivative of a first Bronsted acid and a second Bronsted acid wherein the vinyl product ester is less volatile than the vinyl reactant ester. In particular, Mokhtarzadeh, et al. teaches reacting vinyl acetate and benzoic acid to produce vinyl benzoate or reacting vinyl acetate with 2-ethylhexanoic acid to produce vinyl 2-ethylhexanoate. See, particularly, Examples 4 and 8. Mokhtarzadeh, et al. further provides for removal of the reaction product from the column to avoid reflux and thus aid the reactive distillation process; reactants are recycled to the reactor. Ruthenium catalyst concentrations of from about 30,000 ppm to about 0.01 ppm based on the weight of the liquid phase reaction medium and reaction temperatures of from about 20° C. to about 300° C. are disclosed, with a ruthenium concentration of 50-75 ppm and a temperature of 125-135° C. disclosed in Examples 4 and 8, and a temperature of 140-145° C. disclosed in Example 3. However, the Mokhtarzadeh process achieves poor yields.

U.S. Pat. No. 6,891,052 to Tanner et al. teaches formation of a vinyl ester using a zinc carboxylate catalyst and acetylene gas. Tanner et al. teaches batch operation at a temperature of about 205° C. See Examples 1 and 2, which exemplify synthesis of vinyl neodecanoate.

European Patent No. 0648734 A1 to Packett discloses synthesis of higher vinyl esters directly from ethylene in the presence of palladium cupric salt catalysts, but achieves very low yield. See Examples 2-11, 22, 26-27, 29-32, 36-39 and 41-43, wherein vinyl 2-ethylhexanoate is prepared at yields of up to 69%; Example 12 which discloses production of vinyl butyrate; Examples 18, 25 and 34, wherein synthesis of vinyl neodecanoate is disclosed in yields up to 37%; Examples 19 and 35, wherein synthesis of vinyl benzoate in yields of 21% is disclosed; Examples 20-21, in which synthesis of a mixture of vinyl adipate compounds having a combined yield of up to 46% is disclosed.

U.S. Pat. No. 5,223,621 and EP 0 494 016 B1 to Vallejos et al. teach transvinylation of carboxylic acids, including benzoic acid, with VAM in the presence of a catalyst and ligand in a system that incorporates reflux. Vallejos et al. disclose a palladium acetate (II)—2,2'-bipyridyl complex catalyst formed in situ in a mole ratio of 2,2'-bipyridyl to palladium (II) acetate of about 3:1. See particularly Examples 6 and 8. In example 8, Vallejos et al. describes using 8721 ppm of palladium equivalent per kg of benzoic acid and a VAM to acid ratio of 5:1. After a reaction time of 6 hours, the process according to Vallejos et al. achieved a yield of 89%. The transvinylation reaction disclosed by Vallejos et al. provides a TON of 0.12 kg VB/g Pd. However, the combined use of palladium (II) acetate and 2,2'-bipyridyl is only described in Example 6. The catalyst recovery taught by Vallejos et al. involves precipitation and filtration of palladium from the reaction medium, after which the product is removed by distillation. The temperature of the reaction is held at or below 100° C. to maintain catalyst stability.

U.S. Pat. No. 5,214,172 to Waller discloses catalytic transvinylation of a carboxylic acid to form a vinyl ester. Waller further teaches reactants including vinyl acetate and aliphatic and aromatic mono-carboxylic acids reacted in the presence of a palladium catalyst introduced to the reaction mixture as palladium acetate complexed with an aryl N-containing ligand, such as 2,2'dipyridyl or 1,10-phenanthroline. However, Waller only provided working examples for transvinylation of stearic acid and dicarboxylic acids including suberic, adipic, glutaric, and succinic acids, and found the catalyst complexes having 2,2'-dipyridyl or 1,10-phenanthroline ineffective for use with dicarboxylic acids.

U.S. Pat. No. 5,741,925 to Mao et al. teaches transvinylation of naphthenic acids, which are classified as monobasic carboxylic acids of the formula $C_nH_{2n-z}O_2$, where n indicates the carbon number and z is zero for saturated acyclic acids and 2 for monocyclic acids, for example, with a vinyl ester, such as vinyl acetate. The process of Mao et al. is directed primarily to $C_{10}$ to $C_{20}$ carboxylic acids, as evidenced by claims 2 and 8. Catalysts used in the transvinylation process of Mao et al. include palladium acetate complexed with one or more aryl N-containing ligands, such as 1,10-phenanthroline or 2,2'-dipyridyl. Mao et al. further teaches that the catalysts can be recycled over several uses.

From the foregoing, it is clear that the existing processes utilize toxic catalysts such as mercury catalysts and/or are not appropriate for economically viable industrial scale operations. Furthermore, there is an unmet need for economically viable catalysts that produce vinyl esters with high selectivity, high conversion and in short reaction campaign times from the reaction of VAM and other carboxylic acids in a continuous or semi-continuous operation.

SUMMARY OF THE INVENTION

The new continuous transvinylation process described in the present invention will result in a more economical route to vinyl ester monomers compared to conventional batch reaction setups.

There is thus provided in a first aspect of the invention a continuous process for selective formation of a vinyl ester from its corresponding carboxylic acid. In the formation process, a carboxylic acid and vinyl acetate are continuously fed to a reactor and reacted in the presence of a homogeneous transvinylation catalyst in a reaction mixture to form a vinyl ester product and acetic acid. Acetic acid and vinyl acetate are preferably continuously removed from the reaction mixture and at least a portion of the vinyl acetate is separated from the acetic acid and recycled to the reaction mixture. A crude vinyl ester product mixture may be continuously withdrawn and residual carboxylic acid, residual vinyl acetate, residual acetic acid, and homogeneous transvinylation catalyst are separated from the crude vinyl ester product mixture to form a purified vinyl ester product.

The process of the invention is characterized in various embodiments by a conversion of carboxylic acid to vinyl ester product with a selectivity of at least 80 mole %, less than 15 weight % acetic acid in the crude product mixture, and a molar ratio of vinyl acetate:carboxylic acid of from 1:1 to 6:1 maintained in the reaction mixture. These characteristics are achieved by selection of catalyst and carboxylic acid reactant and by controlling the esterification reaction conditions, feed to the reaction mixture, removal of acetic acid from the reaction mixture, and the separation and recycling of vinyl acetate to the reaction mixture.

Other aspects and advantages of the present invention are described in the detailed description below and in the claims.

BRIEF DESCRIPTION OF THE DRAWINGS

The invention is described in detail below with reference to the appended drawings, wherein like numerals designate similar parts. In the Figures.

DETAILED DESCRIPTION OF THE INVENTION

Figure 1:
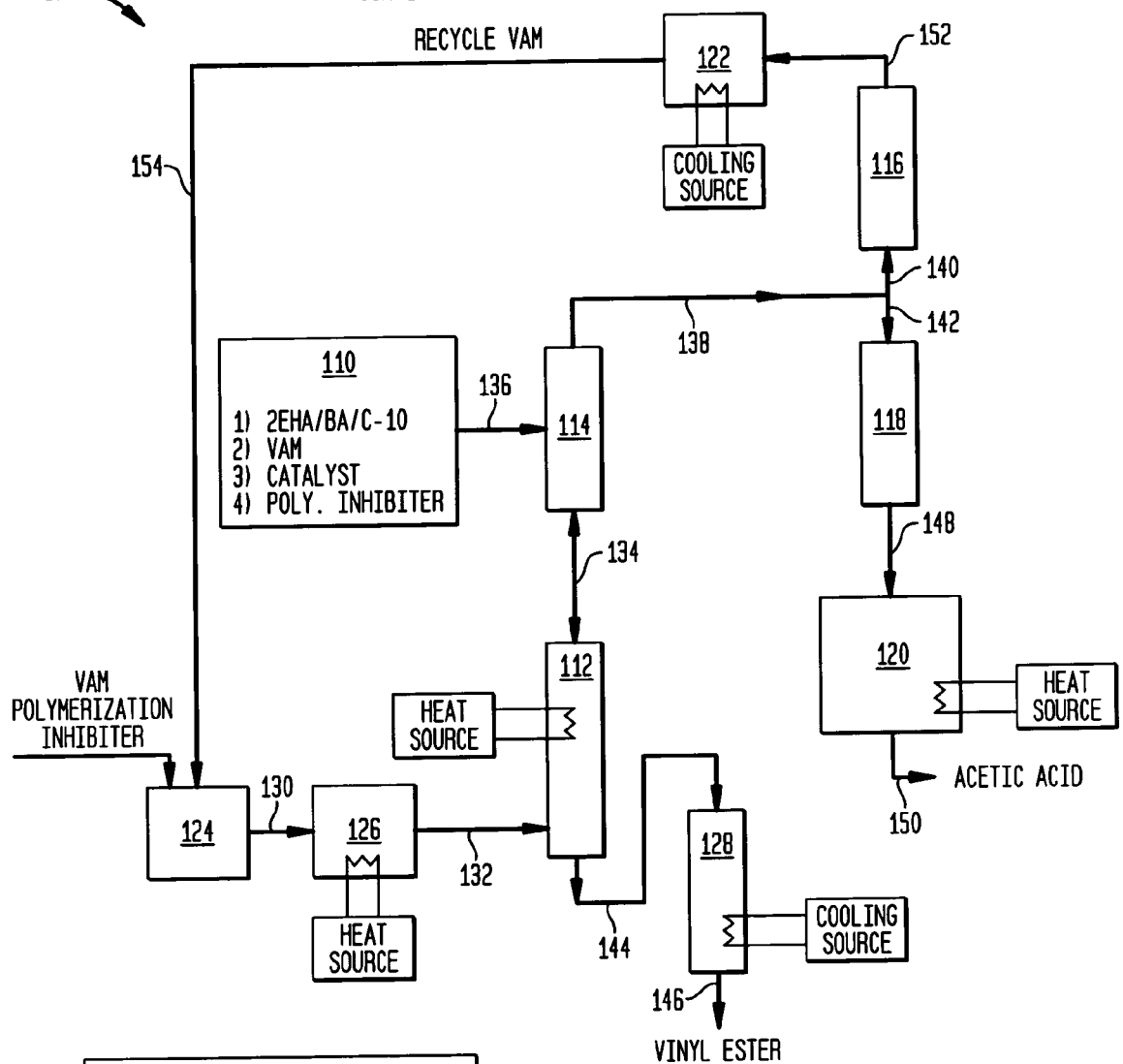
FIG. 1 is a process flow diagram illustrating a continuous reactive-distillation apparatus suitable for the production of vinyl esters.

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below.

Percent, % and so forth refers to mole percent, unless the usage or context clearly indicates otherwise.

The transitional phrase "consisting essentially of" limits the scope of a claim to the specified materials or steps "and those that do not materially affect the basic and novel characteristic(s)" of the claimed invention. As used herein with respect to process claims, "consisting essentially of" means that the steps are carried out in the recited sequence and exclude steps therebetween that involve substantial reaction of an intermediate or final product; for example, intermediate steps would not involve reaction of more than about 10% of the intermediate product. With respect to product claims, "consisting essentially of" and like terminology refers to the recited components and excludes other ingredients which would substantially change the basic and novel characteristics of the composition or article. Unless otherwise indicated or readily apparent, a composition or article consists essentially of the recited components when the composition or article includes 90% or more by weight of the recited components. That is, the terminology excludes more than 10% unrecited components.

"Platinum group metal" means and includes iridium, osmium, palladium, platinum, rhodium and ruthenium.

As used herein, the reference to palladium content is differentiated from catalyst or catalyst complex content in that palladium content refers to the weight or mole fraction of the catalyst or catalyst complex that is palladium metal atoms.

"Selectivity" refers to the amount of vinyl ester produced relative to the carboxylic acid consumed and is expressed as a mole percent based on converted carboxylic acid. Selectivity to vinyl ester (VE) is calculated from gas chromatography (GC) data using the following equation:

$$\text{Selectivity to } VE(\%) = 100 * \frac{\text{mole } VE, \text{out } (GC)}{\text{mole } CA, \text{in-mole } CA, \text{out } (GC)}$$

Where mole CA, in=mole of carboxylic acid loaded into the reactor, mole CA, out (GC)=mole of carboxylic acid after the reaction based on GC data, and mole VE, out (GC)=mole of vinyl ester after the reaction based on GC data.

"Conversion" refers to the fraction of reactant consumed in the reaction and is expressed as a mass percentage based on the initial carboxylic acid (reactant) in the feed. The conversion of carboxylic acid (CA) is calculated from gas chromatography (GC) data using the following equation:

$$CA \text{ converstion } (\%) = 100 * \frac{\text{mass } CA_{fee} - \text{mass } CA, \text{out } (GC)}{\text{mass } CA_{feed}}$$

Where mass $CA_{feed}$=mass of carboxylic acid loaded (weighed in) into the reactor, and mass CA, out (GC)=mass of carboxylic acid after the reaction based on GC data.

"Yield" refers to the amount of carboxylic acid converted to vinyl ester formed and may be determined using the following equation:

$$\text{Yield } (\%) = \frac{\text{selectivity} \times \text{conversion}}{100}$$

where selectivity and conversion are determined as disclosed above. Alternatively, yield may be determined by dividing the moles of ester formed by the moles of carboxylic acid fed, multiplied by 100.

The catalyst activity may be determined herein by turn over number (TON) using the following equation:

$$TON = \frac{\text{kg product formed over one or more production cycles}}{\text{g of } Pd \text{ from the initial charge}}$$

TON generally refers to the average amount of desired product produced by each metal atom contained in the catalyst while the catalyst charge remains active. The term "g of Pd" refers to the initial palladium mass charged to the reactor which is recycled back to the reactor for each production cycle. For a continuous process, TON is calculated as kg product formed until falling conversion or selectivity values indicate that significant amounts of catalyst have been rendered inactive. TON may also be calculated as kg product formed per g of palladium fed over a specified period of time under steady state operation. As used herein, initial TON for a continuous reactor operated at steady-state conditions refers to the product formed per g of palladium fed for a duration of five times the residence (or hold-up) time, unless otherwise indicated.

Hourly Catalytic Productivity as used herein for the continuous transvinylation process refers to the rate of formation of the product as a function of the amount of catalyst used in one hour and is analogous to a space-time yield. Hourly Catalytic Productivity is reported in kg vinyl ester per hour per gm catalyst metal and is calculated as follows:

Hourly Catalytic Productivity=

$$\frac{\text{formation rate of } VE \text{ from reactor} \times 1000 \text{ g/mg}}{\text{conc. of catalyst metal} \times \text{mass } CA_{feed}}$$

Where formation rate of vinyl ester from the reactor is measured e.g., in kg per hour; mass $CA_{feed}$=feed rate of carboxylic acid loaded (weighed in) into the reactor (e.g., kg per hour); and concentration of catalyst metal is reported in ppm based on the feed rate of carboxylic acid. Alternatively, Hourly Catalytic Productivity may also be calculated as follows:

$$\text{Hourly Catalytic Productivity} = \frac{TON}{\text{Total reaction time, hr}}$$

Where total reaction time as used herein refers to a multiple of the reactor residence time, typically five times the residence time for purposes of the Examples. This reaction time allows for unattended operation of a steady state reaction with no catalyst deactivation.

As used herein, the term "reaction mixture" refers to the liquid mass in the reactive distillation area that contains reagents, catalyst, and optionally solvent.

As used herein, the term "reactor residence time" refers to the average amount of time a discrete quantity of reagent spends in the reactor. The mean residence time is determined by dividing the reactor volume by the volumetric flow rate of the carboxylic acid mixture fed to the reactor.

As used herein, the reaction temperature refers to an average of multiple temperature readings taken at various points between the location of the carboxylic acid feed and the vinyl acetate feed. Preferably, at least two temperature readings are averaged, and more preferably, at least three temperature readings are averaged.

Various carboxylic acids known in the art can be employed in the process of this invention to form corresponding vinyl esters. The acids that are suitable in this invention may include, but not necessarily be limited to, the following acids:
2-ethylhexanoic acid, benzoic acid, neodecanoic acid, propionic acid, butyric acid, valeric acid, heptanoic acid, acrylic acid, methacrylic acid, stearic acid, and palmitic acid.

Preferably, the vinyl esters produced in the process of this invention include vinyl 2-ethylhexanoate (V2EH), vinyl benzoate (VB), vinyl neodecanoate (NAVE-10), vinyl propionate, vinyl butyrate, vinyl valerate, vinyl heptanoate, vinyl acrylate, vinyl methacrylate, vinyl stearate, and vinyl palmitate.

The transvinylation process can alternatively be practiced with a carboxylic acid and a vinyl ester other than vinyl acetate as raw materials, or with a carboxylic acid and mixtures of vinyl esters. Suitable vinyl esters include all of the above-mentioned vinyl esters as well as the homologous series of each above-mentioned vinyl ester and fatty acid esters, for example vinyl laurate.

Neodecanoic acid is a member of the neo acid family. Neo acids are highly branched aliphatic carboxylic acids. In general, neo acids are trialkyl acetic acids, which include a tetra substituted alpha-carbon. Alkyl groups on the substituted alpha-carbon create a steric effect, i.e. hinder the ability of the neo acid to react. Methyl substituted alpha-carbon neo acids are the least hindered of the neo-acids. The reactivity of the neo acid primarily depends on the molecular weight and structure of the neo acid. In general, the greater the molecular weight of the alkyl groups on the alpha-carbon, the greater the steric effect and the less reactive the neo acid. Neodecanoic acid in particular is a mix of isomers of $C_{10}H_{20}O_2$ having an average molecular weight of approximately 172 grams/mole. Two examples of such isomers are shown below.

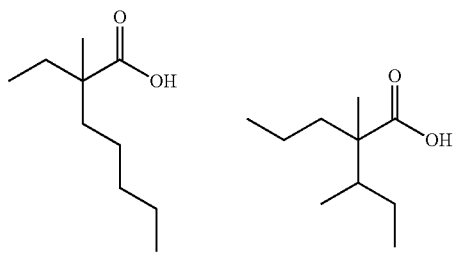

A vinyl ester of the present invention is derived from a neodecanoic acid that has the following general structure:

Formula I

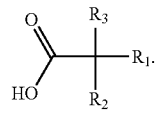

where $R_1$ and $R_2$ are alkyl groups which together may typically collectively contain about 7 carbon atoms, that is, on average, and $R_3$ is generally a methyl group. Vinyl neodecanoate refers to a vinyl ester of a saturated, branched monocarboxylic acid having an average of 10 carbon atoms in the acid radical.

The process according to the invention includes reactive distillation at reflux temperature as a fully continuous process. A carboxylic acid, such as 2-ethyl hexanoic acid (2-EHA), benzoic acid (BA), or neodecanoic acid (C-10); vinyl acetate; and a palladium acetate (II)—2,2'-bipyridyl catalyst complex are charged continuously to a reactor. Byproduct acetic acid formed during the reaction is continuously removed from the reactor as a vapor along with vinyl acetate vapor. The byproduct vapor is routed through a fractionation assembly to recover excess vinyl acetate, which is recycled back to the reactor. Excess vinyl acetate is recovered by distillation at atmospheric pressure or mild vacuum (e.g., about 500 to 760 mm Hg). Byproduct acetic acid is subsequently recovered by vacuum distillation. Finally, product vinyl ester is recovered under reduced pressure. Catalyst and unconverted carboxylic acid remain, with a very small amount of product, providing at a minimum 15 catalyst recycles per reaction time. Vinyl ester recovered from this process is generally at least 95% pure. Trace amounts of acetic acid may remain. This process achieves higher productivity. The transvinylation reactions are generally described by the representative chemical formulas shown below.

Formula II

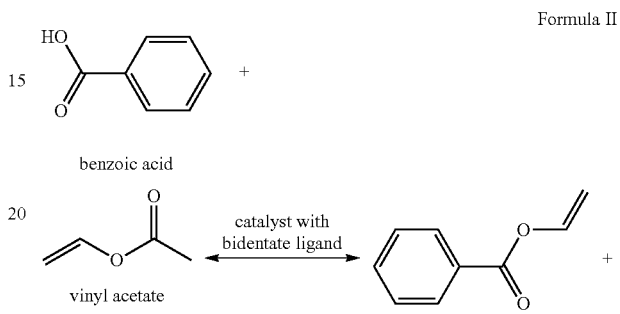

Formula III

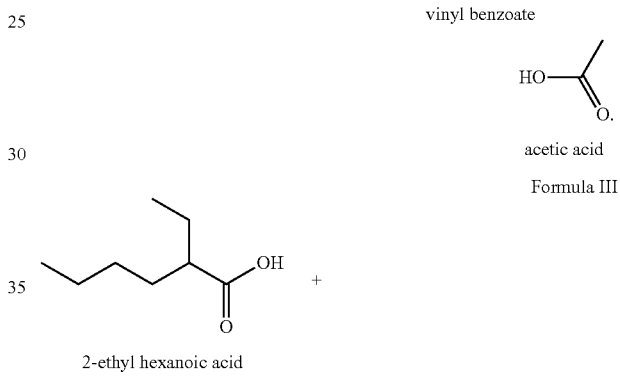

Formula IV

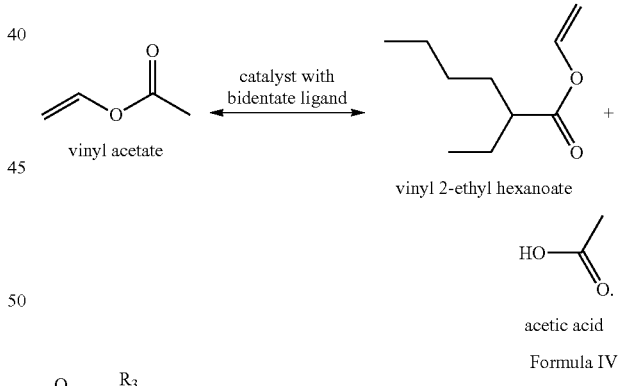

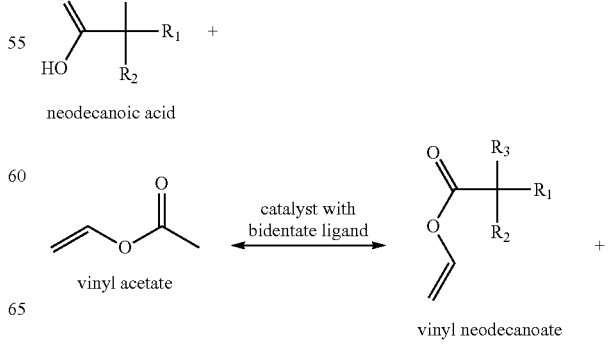

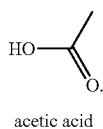

acetic acid

Catalyst Preparation.

Several catalysts may be used for transvinylation, as disclosed by McKeon et al., Tetrahedron, Vol. 28, pp. 227-238, 1972. These catalysts may include simple Pd (II) salts of strong acids such as $PdCl_2$, and Pd(II) salts of weak acids, such as Pd(II) acetate, complexed with monodentate or bidentate ligands, such as pyridine, triethylphosphine, triphenylphosphine, 2,2'-bipyridyl, and 1,10-phenanthroline. Cis palladium acetate complexes have shown to be particularly stable, and bidentate ligands have shown to be more effective than monodentate ligands. Some examples of effective catalysts include diacetato(2,2'-bipyridyl)palladium(II), diacetato(1,10-phenanthroline)palladium(II), diacetato-(N,N,N',N'-tetramethylethylenediamine)palladium(II) and diacetato(P,P,P',P'-tetraphenyl-1,2-diphosphinoethane)palladium(II). The catalyst is prepared separately from the reactive distillation process using standard procedure as reported in JCS (T. A. Stephenson, (Mrs.) S. M. Morehouse, A. R. Powell, J. P. Heffer, and Wilkinson, J. C. S., 3632-3640 (1965)).

Continuous Removal of Acetic Acid from the Reaction Zone.

Acetic acid is removed continuously out of the reaction zone with the help of VAM to shift the equilibrium of Formula II or Formula III, above, to the right. A binary mixture of acetic acid and VAM reduces the temperature at which acetic acid vaporizes, allowing acetic acid removal at a temperature below the deactivation temperature of the catalyst used in the invention. More than about 90 wt % to 95 wt % of the acetic acid formed is removed from the reaction zone.

VAM Recycling and Use of Lower VAM Concentrations.

VAM is distilled out and supplied back to the reaction zone allowing use of a lower molar ratio of VAM/reactant carboxylic acid than is disclosed in the prior art. With the process according to the invention, the amount of VAM required approaches a theoretical ratio based on stoichiometry and thus reduces or eliminates the need for excess VAM in the reaction zone. The molar ratio of VAM to carboxylic acid in the reaction zone ranges from at least 1:1 up to less than 9:1.

Conversion Rates.

Generally, a minimum of 60 wt % of the carboxylic acid charged is converted to vinyl ester. Product selectivity is more than 99 mol %, based on the carboxylic acid charged to the reaction. The turnover number (TON) achieved was at least 20 kg of vinyl ester per gram of palladium without deactivation of the catalyst.

Reactor Designs.

A conventional reactive distillation column (RXDC) may be used in the continuous process according to the invention. In the continuous process, the carboxylic acid and catalyst are continuously fed to the reaction zone in a counter current fashion to VAM/VA and by-product acetic acid is removed continuously with excess VAM/VA, which helps to shift the reaction equilibrium to the right (see Formulas II and III, above). The vinyl ester product is continuously removed at the bottom of the reaction zone and subjected to recovery of product and catalyst. This helps to achieve high throughput of the reactor, reduces equipment size and capital cost, improves acetic acid removal efficiency, and reduces inventory of various reactants. In this approach, reaction residence time is low, and thus the catalyst and vinyl ester product are exposed to heat for a minimal period. This helps to maximize production across the vinyl ester unit.

Reflux Ratios and Flow Rates.

The process according to the invention allows the use of minimized reflux ratios in the reaction zone columns. VAM recovered from the process is 99.9% pure and can be immediately reused in the reaction. VAM recycle ratios range from about 0.5:1 to about 7:1.

Catalyst Concentration.

An amount of catalyst providing about 150 ppm to about 2325 ppm equivalent palladium is provided based on the mass of carboxylic acid reactant. Preferably, the concentration of catalyst metal is from 250 ppm to 2000 ppm, and in some embodiments, from 500 to 1000 ppm of palladium. Palladium (Pd) concentrations below 250 ppm Pd were achieved while maintaining conversion values above 70 wt %, for example, concentrations as low as about 130 ppm Pd were achieved. Ruthenium (Ru) on an active carbon support may alternatively be used as a heterogeneous catalyst.

Reactive Distillation Continuous Feed.

The tubular system provided in a reactive distillation column allows a lower reaction mixture residence time, and improved acetic acid stripping efficiency than may be achieved by reactor designs disclosed in the prior art. While not being bound by theory, a higher TON may also be achieved due to better thermal protection of the catalyst.

Reaction Conditions.

Reaction temperatures of a process according to the invention are lower than conventional processes. The reaction is performed at atmospheric pressure. The reaction temperature may range from about 80° C. to about 120° C. Preferably the temperature of the reaction is maintained from about 90° C. to about 110° C. However, low catalyst concentrations require higher reaction temperatures. The molar ratio of vinyl acetate to the reactant carboxylic acid charged to the reactor is about 2.2:1 to about 9:1. Ratios may be less than about 4:1, and ratios of less than 2:1 have been achieved in some cases. The reaction time ranges from less than about 3 hours to about 36 hours depending upon the catalyst concentration and acetic acid removal rate.

Continuous Inhibitor Addition.

An inhibitor is added to the reaction and to the crude and purified products to prevent vinyl ester polymerization. Without inhibitor addition, side reactions may occur resulting in homopolymers or copolymers of the vinyl ester reactant and/or product. Such reactions impact quality and yield and have adverse safety implications. Any suitable inhibitor may be used, such as hydroquinone (HQ), methoxy hydroquinone (MeHQ), butylated hydroxytoluene (BHT), tert-butyl catechol (TBC), or phenothiazine.

Coproduction of Acetic Acid-VAM Mix.

This process produces a mixture rich in acetic acid. This mixture is drawn off from the process and may be utilized directly or with minimal processing in VAM plants. Alternatively, acetic acid may be separated from the mix. Byproduct acetic acid may be used as a reactant in subsequent processes. Experiments using the Pd catalyst complex of the invention resulted in VAM:acetic acid molar ratios ranging from 0.5:1 to 14.4:1 in the recovered mixture. Preferably, the vinyl acetate:acetic acid molar ratio removed from the reaction mixture is from about 1.5:1 to about 10:1 or about 1:1 to about 9:1. More preferably, the process results in a molar ratio of VAM:acetic acid of from about 2:1 to about 7:1; and even more preferably, the process results in a molar ratio of VAM:acetic acid 2.5:1 to 6:1.

Purification of Carboxylic Acid Reagent.

Surprisingly, in some cases, carboxylic acid reagents demonstrating otherwise high levels of purity have been found to contain impurities that cause deactivation of the catalyst during transvinylation. These impurities may include compounds having alcohol functional groups; compounds having ester functional groups; compounds having olefinic functional groups; compounds having peroxide functional groups; sulfur; and other electropositive metals. It has been further surprisingly discovered that a number of purification methods may be effective in reducing these impurities. These methods may include flash distillation; fractionation; extraction, e.g., water wash (i.e., multistage extraction); hydrogenation; and combinations thereof. Preferably, the purification method includes at least extraction, wherein the carboxylic acid is repeatedly water washed for from about ½ hour to about 2 hours and subject to phase separation. In some embodiments, the purification method is hydrogenation followed by water wash. The catalyst selected for hydrogenation remains active for at least 50 cycles of hydrogenation, and may be palladium on a carbon support. The purified carboxylic acid may be distinguished from impure, or crude, carboxylic acid in that it is characterized by a bromine value of less than 20 mmoles of $Br_2/g$, preferably 18 mmoles of $Br_2/g$ or less, and still more preferably less than 10 mmoles of $Br_2/g$; a peroxide value of less than 200 ppm, preferably less than 100 ppm, and still more preferably less than 20 ppm; or a permanganate time of more than 30 minutes, preferably more than 60 minutes and most preferably more than 120 minutes.

EXAMPLES

Examples 1-7

(Invention): Continuous Operation

Utilizing the materials, techniques, and amounts described generally further below, the process of the invention was operated continuously using a reactive distillation column (RXDC), of the class illustrated in FIG. 1. The catalyst used was diacetato palladium (II)-2,2'-bipyridyl complex.

The continuous reactive distillation apparatus is best shown in FIG. 1. The apparatus 100 comprises a carboxylic acid feed vessel 110; a transvinylation reactor 112, such as a tubular bubble column, provided with an additional packed column 114 placed on top of the reactor 112; a rectification column 116; a stripping column 118; a reboiler 120; a condenser 122; a VAM feed vessel 124; a VAM pre-heater/vaporizer 126; and a product cooler 128.

A pre-mixed feed of CA, VAM and catalyst from the carboxylic acid feed vessel 110 was charged to column 114 via line 136. VAM from VAM feed vessel 124 was passed through preheater 126 via line 130. The CA along with catalyst flowed downward through column 114 to bubble column reactor 112 via 134, countercurrent to superheated VAM vapor, introduced to the reactor 112 via line 132 from preheater 126, which rose upward through bubble column reactor 112 and subsequently column 114 via 134. The reaction took place in the bubble column reactor 112 as well as in column 114, producing vinyl ester and acetic acid. The VAM vapor became saturated with acetic acid. The combined vapors of VAM & acetic acid emitted out of column 114 via line 138 and entered between columns 116 and 118, a separation system where VAM & acetic acid are continuously separated. Line 140 indicates lighter components rising through the rectification portion of the separation system represented by column 116 and line 142 indicates heavier components falling through the stripping portion of the separation system represented by column 118. The product vinyl benzoate or vinyl-2-ethyl hexanoate along with catalyst, unconverted CA, residual VAM, and a small amount of acetic acid was continuously removed from the reactor 112 via line 144, cooled in condenser 128, and collected via line 146. Heavier components from column 118 collected in reboiler 120 via line 148. The overflow of reboiler 120 produced acetic acid and was collected in via line 150. Lighter components from column 116 were collected via line 152, condensed in condenser 122, and recycled to VAM feed vessel 124 via line 154.

Procedure:

The bubble column reactor 112 was first charged with a composition comprising vinyl acetate, carboxylic acid, and catalyst, and heated by conventional means to 98 to 102° C. Then the VAM at a predetermined rate was pumped through the VAM pre-heater 126 which was maintained at 70° C. to 100° C., the VAM vapor entered at the bottom of the bubble column reactor 112. As soon as VAM started distilling out from rectification column 116, the addition of pre-mixed feed of CA, catalyst, VAM & inhibitor was started at predetermined feed rate through column 114. The crude product that overflowed out of bubble reactor 112 through product cooler 128 was collected. Similarly the acetic acid overflowed continuously out of reboiler 120 and was separately collected. The excess VAM was continuously recovered and recycled through the condenser 122 to the VAM metering system.

In production of crude vinyl benzoate, a crystallization step might not be necessary in conjunction with reactive distillation, due to the high conversion rate achievable. Crude vinyl ester product produced through the continuous reactive distillation might need less intensive purification than is necessary for a comparable vinyl ester product from a semi-continuous process because all or almost all of the lights (i.e., vinyl acetate and acetic acid) are removed during the reaction.

Optionally, residual carboxylic acid and catalyst recovered from the crude vinyl ester product may be recycled to the reactor.

TABLE 1

Continuous V-2-EH Reactive Distillation Conditions and Performance.

| | Example No. | | |
| --- | --- | --- | --- |
| | 1 | 2 | 3 |
| 2-EHA feed rate, g/h | 2647.7 | 2233.7 | 1322.5 |
| Palladium conc. on 2-EHA basis, ppm | 2310 | 2310 | 2310 |
| Palladium, g/h | 6.12 | 5.16 | 3.05 |
| VAM feed rate, g/h | 1582.5 | 1335.1 | 790.4 |
| Mole ratio of VAM to 2-EHA as fed to reactor | 1.0:1.0 | 1.0:1.0 | 1.0:1.0 |
| Reaction temp., ° C. | 96 to 100 | 96 to 100 | 96 to 100 |
| Reactor Volume based on voidage, L | 4.72 | 4.72 | 4.72 |
| Residence time, h | 4.91 | 5.82 | 9.83 |
| Vinyl ester formed, g/h | 1772.0 | 1533.2 | 976.0 |
| Conversion of 2-EHA, % | 56.69 | 58.14 | 62.51 |
| Selectivity of 2-EHA to V2EH, % | 100% | 100% | 100% |
| Hourly Catalytic Productivity, kg V2EH/h-g Pd | 0.29 | 0.30 | 0.32 |
| Initial Turn Over Number, kg V2EH/g Pd (assuming steady-state operation for a duration of 5 times the residence time) | 7.11 | 8.65 | 15.70 |

TABLE 2

Continuous VB Reactive Distillation Conditions and Performance.

| | Example No. | | | |
|---|---|---|---|---|
| | 4 | 5 | 6 | 7 |
| BA feed rate, g/h | 612.2 | 435.2 | 337.8 | 338.3 |
| Palladium conc. on BA basis, ppm | 1200 | 1200 | 1200 | 1200 |
| Palladium, g/h | 0.73 | 0.52 | 0.41 | 0.41 |
| VAM feed rate, g/h | 1855.3 | 1318.8 | 1023.8 | 1025.3 |
| Mole ratio of VAM to BA as fed to reactor | 4.3:1 | 4.3:1 | 4.3:1 | 4.3:1 |
| Reaction temp., ° C. | 93-95 | 93-95 | 93-95 | 103-105 |
| Reactor Volume based on voidage, L | 4.72 | 4.72 | 4.72 | 4.72 |
| Residence time, h | 7.35 | 10.34 | 13.32 | 13.30 |
| Vinyl ester formed, g/h | 514.2 | 405.6 | 323.0 | 337.6 |
| Conversion of BA, wt % | 69.23 | 76.83 | 78.81 | 82.25 |
| Selectivity of BA to VB, % | 100 | 100 | 100 | 100 |
| Hourly Catalytic Productivity, kg VB/h-g Pd | 0.70 | 0.78 | 0.80 | 0.83 |
| Initial Turn Over Number, kg VB/g Pd (assuming steady-state operation for a duration of 5 times the residence time) | 25.72 | 40.15 | 53.06 | 55.29 |
| Acetic acid concentration in crude product, wt % | 4.2 | 3.3 | 2.7 | 2.3 |

Processing of Reaction Mixture

The reaction mixture was charged to a rotary evaporator (not shown) of a class known to one of skill in the art. VAM and acetic acid were allowed to distill out and were collected. The distillate also contained a small amount of vinyl ester product. For vinyl benzoate, at this point, the hot reaction mass was transferred to a stirred crystallizer (not shown) of a class known in the art.

V-2-EH was allowed to further distill and was separately collected. This distillate mainly contained V-2-EH and a small amount of acetic acid and 2-EHA, and is herein identified as crude V-2-EH. When distillation ceased, the contents were cooled and the vacuum released. The residue was preserved for recycle. This residue contained mainly 2-EHA, a small amount of V-2-EH and the catalyst.

Crystallization of Un-Reacted BA and Recovery of VB

The reaction mass transferred from the rotary evaporator was cooled in the crystallizer and held for several hours. The slurry was removed and filtered over a vacuum filter. The solid, semi-dried cake of BA was weighed, and the solid cake of BA was preserved for recycle in the next cycle. The mother liquor was weighed and transferred to a conventional evaporator (not shown) for recovery of VB.

Vacuum was applied and the temperature was raised. VB was allowed to distill out and was separately collected. The distillate mainly contained VB and a small amount of acetic acid and BA. This is identified herein as crude VB. Recovery continued until solid BA started appearing in the distillation still at which stage recovery ceased.

When distillation stopped, the contents were cooled and the vacuum released. The residue of unreacted BA & catalyst was preserved for recycle. This residue contained mainly BA, a small amount of VB and the catalyst.

Purification of Crude Vinyl Ester

The crude V-2-EH, VB or NAVE-10 was charged to a conventional fractional distillation column (not shown) under vacuum. Around 25 ppm of HQ was added as a stabilizer. The crude mass was heated. Distillate was collected with reflux set to 1. This distillate contained VAM and acetic acid and was recycled to the reactor.

The pressure was increased as the temperature reached the point at which V-2-EH or VB starts distilling. After removing a small initial cut (fore cut), the main pure vinyl ester cut was collected. The fore cut was recycled in the next purification. The heavy ends from purification were removed and preserved for recycle in the next reaction cycle. The pure cut was more than 99.6% pure with respect to V-2-EH, and more than 99.8% pure with respect to VB, and demonstrated low acid values (less than 1) and APHA values (less than 15), among other quality tests.

Methoxy hydroquinone (MeHQ) was added to a weighed amount of pure vinyl ester at a concentration of less than 40 ppm by weight. It was well-mixed and stored in a cool, dry place. Alternative inhibitors may include hydroquinone (HQ), butylated hydroxytoluene (BHT), tert-butyl catechol (TBC), diphenylamine, phenothiazine, or a hindered phenol, for example NALCO™ polymerization inhibitor.

Processing of Reboiler Mixture

Pre-weighed reboiler contents and VAM & acetic acid cuts collected as described above were charged to a conventional fractional distillation unit (not shown). Vacuum was applied and the contents were heated until VAM started distilling out. When the temperature stabilized, VAM collection began under reflux. The distilled VAM was stabilized by adding 30 ppm of HQ. This recovered VAM was recycled to the reactor. Once the VAM cut was over, the pressure was reduced, allowing acetic acid to distill and collect under reflux.

The continuous reactive distillation process resulted in purified products having the following characteristics.

TABLE 3

Continuous transvinylation product analysis.

| | Example No. | | | |
|---|---|---|---|---|
| | 7 | 42 | 3 | 41 |
| Sample | VB (continuous) | VB (semi-continuous) | V2EH (continuous) | V2EH (semi-continuous) |
| Purity By GC | 99.97% (by area) | 99.67% | 99.92% (by area) | 99.69% |
| Colour Apha | 4.372 | <7.5 | 4.306 | <5.0 |
| Moisture | 0.029% | 0.02% | 0.007% | 0.01% |
| Acid Value, Mg Of KOH | 0.0634 | 0.100 | 0.0708 | 0.174 |
| Specific Gravity | 1.066 | 1.066 | 0.866 | 0.871 |

Example 8

Catalyst Preparation

Catalyst was prepared using palladium acetate and a bidentate ligand such as 2,2'-bipyridyl. This catalyst was prepared generally using toluene as the solvent. Palladium (II) acetate was heated in toluene to 80° C. A solution of 2,2'-bipyridyl in toluene was added over a one hour period. The reaction was continued for two to four hours and then the catalyst reaction mixture was cooled. A catalyst complex, having a mole ratio of palladium (II) acetate to 2,2'-bipyridyl of from about 1:1.1 to 1:1.4, precipitated as a solid. The precipitate was filtered, washed with toluene, and dried under reduced pressure prior to use.

Another catalyst was prepared using a different bidentate ligand such as 1,10-Phenanthroline. The solubility of 1,10-Phenanthroline is negligible in toluene even at high temperature. Hence instead of toluene, acetonitrile, a very polar solvent, was used for preparation of the catalyst complex. Alternative solvents that may be used for preparation of a catalyst according to the invention include toluene, acetonitrile, xylene, benzene, hexane, and cyclohexane. The performance of this catalyst was compared with the catalyst prepared by using 2,2'-bipyridyl as the bidentate ligand.

Another set of catalysts were prepared using monodentate ligands such as either pyridine, to prepare a diacetato palladium (II)-bis-pyridyl complex, or quinoline, to prepare a diacetato palladium (II)-bis-quinolinyl complex. In both cases toluene was used as the solvent. When pyridine was used as the monodentate ligand, the catalyst could not be isolated in powder form, so it was used in solution with toluene. The quinoline-containing catalyst was successfully isolated. The catalyst complexes were tested and compared with the use of bipyridyl complex.

The palladium content for each experiment, expressed in ppm, based on the mass of carboxylic acid charged, was calculated according to the following equation.

$$Pd\ concentration = \frac{[\text{catalyst weight, mg}] \times [\text{ratio of } Pd \text{ MW to Complex MW}]}{[\text{weight of carboxylic acid, kg}]}$$

Examples 9-12

Effect on Transvinylation Reaction Using Catalyst Prepared with Bi-Dentate Ligand A catalyst was prepared by using 1,10-phenanthroline as bi-dentate ligand. The catalyst prepared was a diacetato-palladium (II)-1,10-phenanthroline complex. The catalyst was isolated in solid form, dried and used in the reaction.

A V-2-EH run was performed with a palladium concentration of 626 ppm based on the mass of 2-EHA in a batch system. After six hours running at 100° C., the conversion achieved was 84.26%. A VB run was also performed with a palladium concentration of 626 ppm based on the mass of BA in a batch system. After six hours running at 100° C., the conversion achieved was 75.56 wt %. In both runs, vinyl acetate was provided in a molar vinyl acetate:carboxylic acid ratio of 4:1. The catalyst performance for each run was at par with the catalyst prepared by using a bi-dentate bipyridyl ligand.

TABLE 4

Ligand effect on transvinylation.

| | Example No. | | | |
|---|---|---|---|---|
| | 9 | 10 | 11 | 12 |
| Ligand | Bis-pyridyl complex | Bis-pyridyl complex | 1,10-phenanthroline | 1,10-phenanthroline |
| Carboxylic Acid | BA | 2-EHA | BA | 2-EHA |
| Reaction volume, Liters | 2.01 | 1.83 | 2.01 | 1.83 |
| Pd concentration, ppm | 1230 | 1193 | 626 | 626 |
| Maximum conversion of CA, wt % | 49.98 | 23.35 | 75.56 | 84.26 |
| Time required to attain max. conversion, hr | 9.3 | 7 | 6 | 6 |
| Moles of product formed in above time, gm mol | 2.05 | 0.81 | 3.1 | 2.93 |
| Product formation rate, gm mol/gm Pd per hr | 0.36 | 3.64 | 1.65 | 1.56 |
| Product formation rate, kg/liter reactor volume-hr | 0.016 | 0.011 | 0.038 | 0.045 |

Note:
Bis-quinolinyl complex is not represented in the above table because the reaction was unsuccessful.

Examples 12-19

Catalyst Testing in a Semi-continuous Unit

The catalyst complex (diacetato-palladium (II)-2,2'-bipyridyl) for preparation of V-2-EH in reactive distillation (semi-continuous setup) was recovered with the vinyl ester product and the catalyst was recycled for seven times after recovery. The palladium concentration used per lot of 2-EHA (432 gm 2-EHA per pass) was 2325 ppm based on the mass of 2-EHA. Vinyl acetate was provided in a molar ratio of VAM:2-EHA of 6.2:1. The time required for 75 wt % conversion was less than three hours. As shown in Table 5, below, turnover number (TON) steadily increases with additional cycles and the catalyst remains active.

TABLE 5

Effect of catalyst recycling on reactive distillation transvinylation using 2-EHA to V-2-EH.

| Example No. | 12 | 13 | 14 | 15 | 16 | 17 | 18 | 19 |
|---|---|---|---|---|---|---|---|---|
| Type of run | Fresh catalyst | First recycle | Second recycle | Third recycle | Fourth recycle | Fifth recycle | Sixth recycle | Seventh recycle |
| Moles of 2-EHA | 3.0 | 3.0 | 3.0 | 3.0 | 2.75 | 2.65 | 2.41 | 2.08 |
| Catalyst | Note-1 | Note-2 | Note-2 | Note-2 | Note-2 | Note-2 | Note-2 | Note-2 |
| Palladium conc., ppm | 2325 | 2325 | 2325 | 2325 | 1517 | 1574 | 1724 | 2006 |
| Reaction temperature | 87 to 88° C. | 87 to 88° C. | 92 to 94° C. | 92 to 94° C. | 92 to 94° C. | 92 to 94° C. | 92 to 94° C. | 92 to 94° C. |
| Final conversion of 2-EHA | 76.29% | 70.24% | 70.04% | 79.76% | 74.61% | 70.6% | 70.06% | 69.93% |
| Time in hrs. | 3.0 | 3.0 | 3.5 | 3.0 | 4.5 | 4.5 | 3.5 | 3.0 |
| TON, kg V-2-EH/g Pd | 0.389 | 0.747 | 1.104 | 1.5107 | 1.8905 | 2.42 | 2.898 | 3.310 |

Note-1 -
Catalyst used was Diacetato Palladium (II) -2,2'-bipyridyl complex. Fresh charge.
Note-2 -
The catalyst was recovered in the earlier run and recycled in the subsequent runs.

Examples 20-33

Effect of Impurities on Catalyst Testing in a Semi-Continuous Unit

The same catalyst complex (diacetato-palladium (II)-2,2'-bipyridyl) for preparation of vinyl neodecanoate (NAVE-10) in reactive distillation (semi-continuous setup) was recovered with the vinyl ester product and the catalyst was recycled for ten times after recovery. The C-10 feed was not purified prior to reaction. The palladium concentration used per lot of neodecanoic acid (C-10 acid; 200 gm per pass) was maintained at 750 ppm based on the mass of C-10 acid. Distilled vinyl acetate was provided in a molar ratio of VAM:C-10 acid of 6:1. The reaction step was operated in a 5 L autoclave for 10 hours at 100° C. The reaction mixture was cooled, weighed, and sampled for GC analysis. The vinyl ester was then recovered using a rotary evaporator. The residue was recycled for the next reaction cycle. The reaction mixture was replenished with enough C-10 acid to maintain the same amount for each pass, and the catalyst was replenished with 10 ppm for each pass. As shown in Table 6, below, the catalyst deactivated quickly.

TABLE 6

Effect of C-10 acid impurities on semi-continuous transvinylation to vinyl neodecanoate.

| | Example No. | | |
|---|---|---|---|
| | 20 | 21 | 22 |
| Type of run | Fresh | $1^{st}$ recycle | $2^{nd}$ recycle |
| % Yield of NAVE-10 | 80.86 | 75.44 | 22.13 |

The process described for Examples 20-22 was repeated, except that the neodecanoic acid was purified prior to reaction. As shown in Table 7, below, turnover number (TON) steadily increased with additional cycles and the catalyst remained active. Conversion remained stable with subsequent cycles. The highest concentration of acetic acid measured in the product was 6.91 wt % in the tenth recycle.

TABLE 7

Effect of catalyst recycling on reactive distillation transvinylation using C-10 acid to vinyl neodecanoate.

| Example No. | 23 | 24 | 25 | 26 | 27 | 28 |
|---|---|---|---|---|---|---|
| Type of run | Fresh catalyst | First recycle | Second recycle | Third recycle | Fourth recycle | Fifth recycle |
| Moles of C-10 Acid | 1.2 | 1.2 | 1.2 | 1.2 | 1.2 | 1.2 |
| Final formation of NAVE-10 | 75.23% | 74.48% | 74.50% | 74.62% | 73.83% | 73.84% |
| TON, kg NAVE-10/g Pd | 0.24 | 0.48 | 0.72 | 0.96 | 1.20 | 1.43 |

| Example No. | 29 | 30 | 31 | 32 | 33 |
|---|---|---|---|---|---|
| Type of run | Sixth recycle | Seventh recycle | Eighth recycle | Ninth recycle | Tenth recycle |
| Moles of C-10 Acid | 1.2 | 1.2 | 1.2 | 1.2 | 1.2 |
| Final formation of NAVE-10 | 73.27% | 72.83% | 72.39% | 71.76% | 71.44% |
| TON, kg NAVE-10/g Pd | 1.67 | 1.90 | 2.14 | 2.37 | 2.60 |

Examples 34-40A

Neodecanoic Acid Purification

Generally, C-10 acid is available at 99.5-99.9% purity. However, it was discovered that in some cases impurities in the raw carboxylic acid were poisoning the catalyst in successive cycles. These impurities are believed to include dimers, trimers, di-hydric/polyhydric alcohols and esters of nonene formed during production of C-10 acid, as well as impurities introduced with raw materials in the production of C-10 acid. In order to remedy the situation, a process to purify neodecanoic acid by azeotropic distillation and a catalytic hydrogenation process were developed.

Without intending to be bound by any particular theory, it is believed catalyst poisoning occurs by way of a variety of impurities, including olefinic impurities including alkene impurities, alcohol impurities, ester impurities, sulfur and other electropositive metals, oxidizable impurities generally including unsaturated compounds and aldehydes, for example.

Various purification methods are described below and summarized in Table 8. Note that unpurified (crude) C-10 acid is presented as Example 34 for comparison.

The characteristics determined for the purified acids included bromine value and peroxide value. The determination of bromine value is essential for determination of double bond components present in the C-10 acid, while the peroxide value is also necessary to predict catalyst stability. Solutions are prepared and standardized for both procedures as described in steps I) and II) below. The analytical procedures for determining both bromine value and peroxide value are also provided below.

I) Preparation of Solutions

The following solutions are prepared according to procedures known in the art:
A 0.1N solution of sodium thiosulfate.
A 1% Starch Solution in boiled distilled water.
A 10% KI solution in distilled water (10 gms KI in 100 ml water)

II) Standardization: Normality of Thiosulfate Solution 0.05 g $K_2Cr_2O_7$ is dissolved in 50 ml distilled water to which 5 ml concentrated HCl are added. In a conical flask, the potassium chromate solution is added to 20 ml 10% KI solution, and titrated with the 0.1 N sodium thiosulfate solution until a dark reddish color changes to a faint pale color. One to three drops of starch indicator is then added to the flask and titration is continued until the color changes to a faint green fluorescent color. Three such readings are recorded.

Procedure for Determination of Bromine Value

In addition to the solutions prepared as described above, a mixed solution of potassium bromate and potassium bromide comprising about 2.7 gm of $KBrO_3$ and 17.5 gm of KBr in 1000 ml of distilled water is also prepared.

III) Blank Titration 50 ml of water and 25 ml of the potassium bromated/potassium bromide mixture are mixed with 5 ml of concentrated HCl. After 20 minutes in a dark room, 20 ml of 10% KI are added. The mixture is titrated against the 0.1N sodium thiosulfate solution until a dark reddish-brown color changes to a faint reddish-brown color. Then one drop of starch indicator is added, and the solution becomes a dark bluish color. Titration with sodium thiosulfate continues until the solution becomes colorless. This is the end point of the titration.

IV) Sample Titration

In a 250 ml conical flask, 0.1 gm of sample is dissolved in 10 ml of methanol. To this solution, 50 ml of water, 25 ml of $KBr/KBrO_3$ mixture and 5 ml of concentrated HCl is added. After 20 min in a dark room, 20 ml of 10% KI is added. The solution is titrated with sodium thiosulfate until a dark reddish-brown color changes to a faint reddish brown color. Then one drop of starch indicator is added, and the solution becomes a dark bluish color. Titration with sodium thiosulfate continues until the solution becomes colorless. This is the end point of the titration.

Procedure for Determination of Peroxide Value

III) Blank Titration

In a conical flask, 20 ml of water, 50 ml of MeOH and 5 ml of concentrated HCl are combined with 20 ml of 10% KI and 2 to 3 drops of starch indicator. The solution is titrated with the 0.1 N sodium thiosulfate solution until a pale yellow color becomes colorless. This is the end point of the titration.

IV) Sample Titration

In a 250 ml conical flask, 4 to 5 gm of sample are dissolved in 50 ml of methanol and combined with 20 ml of water, 5 ml of concentrated HCl, 20 ml of 10% KI and 2 to 3 drops of starch indicator. The resultant solution is titrated with the 0.1 N sodium thiosulfate solution until a pale yellow color solution becomes colorless. This is the end point of the titration.

Permanganate Time

Permanganate times are an indication of oxidizable impurities in the feed such as unsaturated compounds, aldehydes and so forth that reduce potassium permanganate. Unless otherwise indicated, permanganate times are measured in accordance with ASTM Test Method D1363-06 at 15° C. with an observation interval of 30 minutes.

(1) Example 35: Flash Distillation (i.e., Flashing)

In the azeotropic distillation purification process, raw neodecanoic acid mixed with a glycol entrainer is fed to a first distillation column. The entrainer forms a hetero-azeotrope with impurities in the raw acid. The hetero-azeotrope of entrainer and impurities is withdrawn from the top of the first distillation column. The impurities are separated from the entrainer by phase separation, and the entrainer is recycled to the first column. Partially purified neodecanoic acid is withdrawn from the bottom of the first distillation column and fed to a second distillation column. Most of the remaining impurities are withdrawn from the top of the second column. The near-pure neodecanoic acid is then fed to a third distillation column for polishing. Purified neodecanoic acid, having a purity of 99.5 to 99.99%, is withdrawn from the top of the third column. Heavy impurities are removed from the bottom of the third column. Note that the permanganate test was negative, indicating that no easily oxidized groups remained. This result was present for all of the purification methods discussed herein.

(2) Example 36: Multistage Extraction (i.e., Water Wash)

Figure 2:
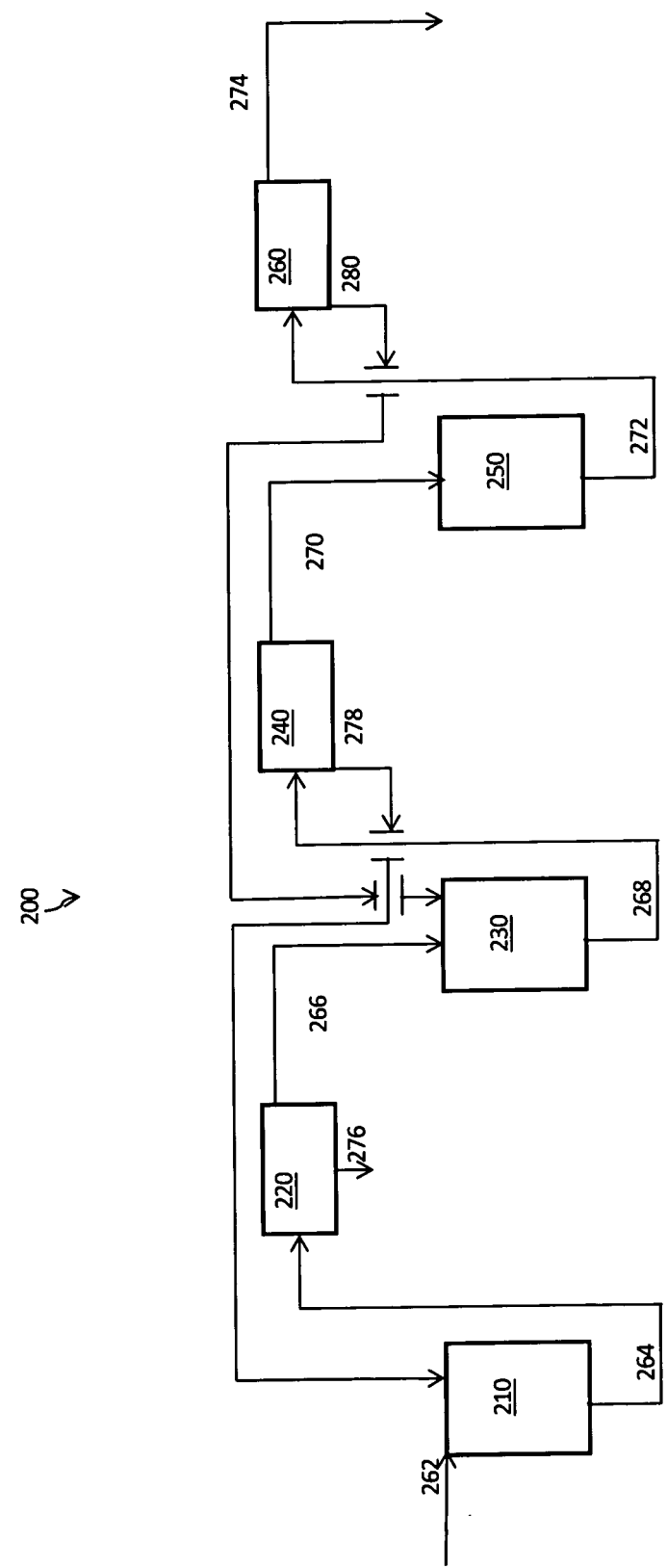
FIG. 2 is a process flow diagram illustrating an embodiment of the invention for purification of a carboxylic acid by extraction.

Water wash removes alcoholic and low boiling impurities by extraction. FIG. 2 illustrates an extraction unit 200 comprising a series of mixing vessels 210, 230, 250 and phase separation vessels, or decanters 220, 240, 260. Three extraction and phase separation steps are shown, but this number of steps is not meant to be limiting. Crude neodecanoic acid was fed via line 262 to the first mixing unit 210 and was agitated with water for 1 hour. The mixture was fed via 264 to the first decanter 220 for phase separation. Spent water was discarded via line 276. The water extraction procedure was repeated about two to three times. As shown in FIG. 2, C-10 acid was transferred from the first decanter 220 to the second mixer 230 via line 266 and subsequently to the second decanter 240 via line 268 and the third mixer 250 via line 270. The C-10 acid was transferred to the final decanter 260 via line 272 and collected from line 274 as purified C-10 acid. The water separated in decanter 260, or raffinate, via line 280, was mixed with C-10 acid in mixer 230, while the water separated in decanter 240, via line 278, was mixed with C-10 acid in mixer 210. The results are summarized in Table 8, below. Note that peroxide value is reduced to zero by this process, but the bromine value is only slightly reduced.

(3) Example 37: Hydrogenation Followed by Fractional Distillation

Alternatively, hydrogenation was applied to convert double bonds in the acid structure to single bonds and then subjected to fractional distillation with acetic anhydride to remove low boiling impurities. In this process, alcohol impurities present are made inactive by acylating them with acetic anhydride and converting them to esters, as shown in the equation below.

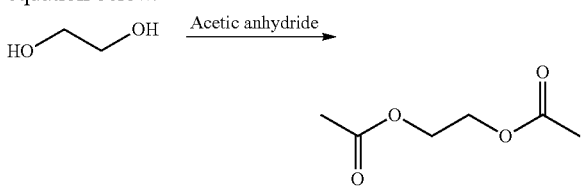

The hydrogenated C-10 acid was charged to a 10 L fractional distillation column. A vacuum of 5 mbar was applied while the temperature was gradually increased from 60 to 125° C. Volatile components were drawn off from the top of the column. The effect on the physicochemical properties of C-10 acid are apparent in the Table below.

(4) Example 38: Hydrogenation Followed by Flashing

In the catalytic hydrogenation process, C-10 acid is reacted in the presence of a 1% Pd/C catalyst to convert any double bonds present in the structure to single bonds, as shown, for example, in the equation below:

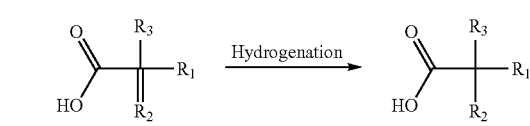

In this process, raw C-10 acid was introduced into a 5 L autoclave to which a known amount of 10% Pd/C catalyst is subsequently added. The mixture is heated for about 8 hours at about 150° C. The C-10 acid recovered from the autoclave was subsequently flashed to remove low-boiling impurities at about 125-127° C. and a vacuum of about 4 mbar in a 3 L rotary evaporator. Catalytic hydrogenation followed by flash distillation achieves dramatic improvements in the physicochemical properties of C-10 acid, as shown in the Table below. Note that the bromine value of the purified acid was zero, indicating that double bond components were converted to single bonds.

(5) Example 39: Hydrogenation Followed by Water Wash

Figure 3:
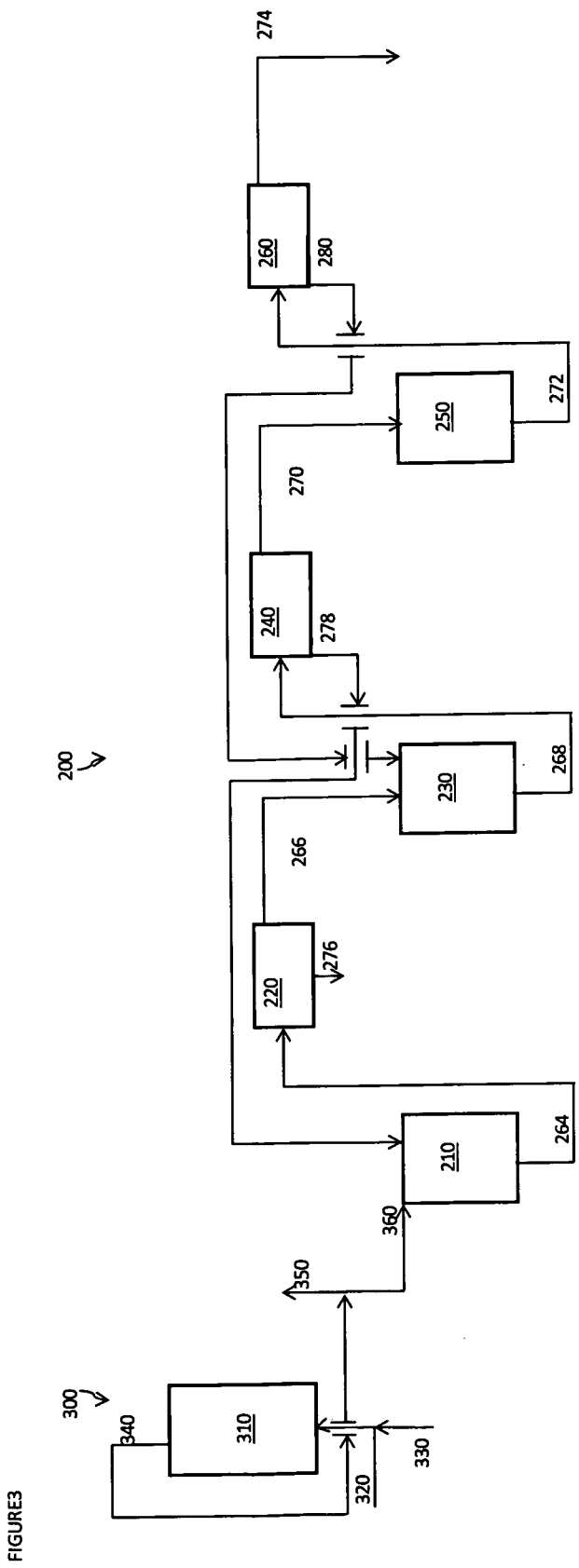
FIG. 3 is a process flow diagram illustrating another embodiment of the invention for purification of a carboxylic acid by hydrogenation followed by extraction.

In this process, structural double bonds and alcohols are removed. As shown in FIG. 3, crude C-10 acid was hydrogenated in a hydrogenation unit 300, comprising a continuous hydrogenator 310 containing a heterogeneous palladium catalyst supported on carbon, followed by extraction, as discussed with respect to Example 36, above. Crude C-10 acid was fed via line 320 with hydrogen via line 330 to the continuous hydrogenator 310. Hydrogenated neodecanoic acid with residual hydrogen was removed from the hydrogenator 310 via line 340. Residual hydrogen was vented at 350, while hydrogenated C-10 acid was sent to the extraction unit 200 via line 360. The C-10 acid was water washed as discussed in Example 36 and illustrated in FIG. 2. The results are shown in Table 8, below. Note that the bromine value and the peroxide value are both reduced to zero.

(6) Example 40: Hydrogenation Followed by Flashing and Water Wash

In this process, structural double bonds, low boiling impurities, and alcohols are removed. Crude C-10 acid was hydrogenated as discussed above. The intermediate purity acid was flashed and then agitated with water for 1 hour. The mixture was fed to a decanter for phase separation. The water extraction procedure was repeated two to three times. The results are shown in the Table below. Note that the bromine value and the peroxide value are both reduced to zero. Subsequent experimentation showed that the hydrogenation catalyst, Pd/C, remained active even after 50 cycles of hydrogenation.

TABLE 8

Summary of physiochemical properties of C-10 acid before and after purification

| Example | 34 | 35 | 36 | 37 | 38 | 39 | 40 |
|---|---|---|---|---|---|---|---|
| Properties | Crude C-10 | Flash distillation | Water wash | Hydrogenation + fractionation | Hydrogenation + flashing | Hydrogenation + water wash | Hydrogenation + flashing + water wash |
| Density (g/L) | 0.9081-0.9137 | 0.9148 | 0.9097 | 0.9075 | 0.9118-0.9124 | 0.911 | 0.9135-0.9141 |
| % Acidity (mg of KOH/g) | 326.52-358.3 | 349.56 | 318 | 336 | 302.91-310.34 | 303.7 | 318.27 |
| Bromine value (mmoles of $Br_2$/g) | 18.22-25.49 | 24.41 | 18 | 0 | 0 | 0 | 0 |
| $KMnO_4$ test | Pink color disappears | | | Pink color does not disappear | | | |
| Peroxide value (ppm) | 232.45-103384 | | 0 | | 0 | 0 | 0 |
| Water (%) | 0.00-0.97 | 0.00 | 0 | 0.07 | 0.13-0.19 | 0.12 | 0.09-0.15 |
| GC Analysis (purity, %) | 99.63-99.78 | 99.99 | 99.859 | 99.50 | 99.91-99.95 | 99.87 | 99.81-99.93 |

Performance Study of Purified C-10 acid on Catalyst Recycle.

Trials were run using the untreated C-10 acid and the purified C-10 acid by various methods to see how purification affected catalyst recycle. The procedure was the same as for Examples 34 through 40, above. The initial C-10 acid charge was 2.32 moles; make-up acid was added to maintain the mass fed to each cycle. The catalyst concentration was 1000 ppm based on the weight of carboxylic acid fed. The results are shown in the Table below.

As apparent in Table 9, above, water wash or water wash following hydrogenation maintained carboxylic acid conversion values surprisingly well in comparison to the other purification methods.

In light of the effects of impurities on catalyst life, a purified C-10 acid is believed essential to the successful production of NAVE-10. Properties of a pure C-10 acid are shown in the Table below.

TABLE 9

Effect of purification method on catalyst performance during recycle.

| | Fresh catalyst % Conversion | $1^{st}$ recycle % Conversion | $2^{nd}$ recycle % Conversion | $3^{rd}$ recycle % Conversion | $4^{th}$ recycle % Conversion | $5^{th}$ recycle % Conversion | $6^{th}$ recycle % Conversion | $7^{th}$ recycle % Conversion | $8^{th}$ recycle % Conversion | $9^{th}$ recycle % Conversion |
|---|---|---|---|---|---|---|---|---|---|---|
| Ex. 34: Untreated | 79.05 | 68.38 | 55.23 | 31.78 | 26 | — | — | — | — | — |
| Ex. 35: Flashing | 70.75 | 64.83 | 48.89 | — | — | — | — | — | — | — |
| Ex. 36: Water wash with 20 ppm catalyst added per recycle | 77.46 | 74.78 | 75.19 | 71.26 | 73.58 | 71.05 | 72.19 | 72.69 | 71.15 | 71.18 |
| Ex. 37: Hydrogenation + fractionation | 75.31 | 73.35 | 70.97 | 67.33 | 62.92 | 59.67 | — | — | — | — |
| Ex. 38: Hydrogenation + flashing | 76.97 | 73.11 | 71.40 | 68.93 | 61.77 | 58.02 | — | — | — | — |
| Ex. 38A: Hydrogenation + flashing with 50 ppm catalyst added per recycle | 74.7 | 70.94 | 71.53 | 70.41 | 66.52 | 64.11 | 46.94 | 54.23 | 44.93 | — |
| Ex. 39: Hydrogenation + water wash with 20 ppm catalyst added per recycle | 76.71 | 75.42 | 74.40 | 74.20 | 72.94 | 73.38 | 72.53 | 72.21 | 72.73 | 72.62 |
| Ex. 40: Hydrogenation + flashing + water wash with 50 ppm catalyst added per recycle | 74.34 | 75.00 | 72.89 | 70.54 | 74.00 | 67.08 | 67.82 | 65.38 | 60.51 | 62.28 |
| Ex. 40A: Hydrogenation + flashing + water wash with 20 ppm catalyst added per recycle | 74.11 | 73.82 | 73.38 | 74.05 | 71.73 | 70.85 | 70.17 | 67.67 | 68.50 | 67.33 |

TABLE 10

Preferred neodecanoic properties for use in the present invention

| Property | Value |
| --- | --- |
| Purity by GLC Method | >99.8% |
| Moisture | Nil |
| Specific gravity | 0.9135 to 0.9345 |
| Melting point | −40° C. |
| Color | <10 APHA |
| Acid value, mg KOH/gm of sample | 320 to 325 |
| Boiling point, ° C. | 262.1 |
| Vapor pressure, mm of Hg | 0.00329 @ 25° C. |
| Distillation range | 147 to 150° C./20 mm of Hg |
| Reducible substances | Nil |
| Peroxides (ppm) | Nil |
| Sulfidic impurities | Nil |
| Heavy metals | <1 ppm |

Examples 41-44

Scale-Up Study & Pilot Runs for V-2-EH, VB and NAVE-10

Transvinylation was performed using a semi-continuous apparatus (not shown) to demonstrate various aspects of the present continuous process.

Carboxylic acid, vinyl acetate, catalyst complex, and hydroquinone were initially charged to a stirred reactor. Vinyl acetate and hydroquinone were initially charged to a stirred reboiler. Depending upon the carboxylic acid selected, a mixture of some or all of vinyl acetate, 2,2'-bipyridyl, carboxylic acid, catalyst complex, and hydroquinone were subsequently charged to the reactor over a period of time. Pure VAM was charged continuously to the top of a small packed column positioned on top of the reactor. Vapors leaving the reactor passed to the first column and subsequently the middle of a second packed distillation column between an upper rectification section and a lower stripping section. From the rectification section, lighter components were collected in a receiver. Heavier components exited the stripping section were collected in the reboiler. Distilled VAM recovered in the receiver was continuously fed to the reactor, which helped to maintain the reaction temperature at about 100 to 101° C. The reaction continued until the desired conversion of CA was achieved. The contents of the reactor (the reaction mass) and the reboiler were removed at the end of the cycle. Unreacted carboxylic acid and vinyl acetate and catalyst were recovered and used in a subsequent cycle. Vinyl ester product was purified as discussed at Table 13. The temperatures of the reactor, distillation column, reboiler and condenser were controlled by conventional means known in the art. Flowrates to the reactor and small column were also controlled by conventional means.

Analysis of the reaction mixture determined that the acetic acid content was below 12 wt % in the production of vinyl benzoate, and less than 10 wt % in the production of vinyl 2-ethyl hexanoate.

The results obtained for V-2-EH and VB using a Diacetato palladium(II), 2,2'-bipyridyl catalyst are shown in Table 11. The results obtained for NAVE-10 using the same catalyst are shown in Table 12. The activity of the catalyst was confirmed by testing a portion of the catalyst separated from the vinyl ester product. The catalyst was combined with a known amount of carboxylic acid and vinyl acetate and maintained at reaction conditions in an autoclave for three hours. A conversion of greater than 30 wt % verified continuing catalyst activity.

TABLE 11

Vinyl ester production reaction performance.

| | Example 41: Vinyl 2-ethylhexanoate production | Example 42: Vinyl benzoate production |
| --- | --- | --- |
| Size of pilot batch, L | 6 kg | 3 kg |
| Conversion of carboxylic acid, wt % | 80.73% | 76.83% |
| Catalyst amount used, Palladium mg | 801.34 | 559.41 |
| Catalyst complex used, mg | 2864.94 | 2000.00 |
| Pd concentration, ppm | 131.54 | 183.78 |
| Moles of carboxylic acid input | 42.31 | 24.95 |
| Amount of product formed, gm mol | 34.16 | 19.17 |
| Reaction time (Initial charge heating + Feeding mixture + Time required to achieve conversion), hr | 39.75 | 41 |
| VAM recycle rate to transvinylation reactor, L/h | 0.5 | 0.8 |
| Average product formation rate, gm mol of vinyl ester/1 gm of Palladium-per hr | 1.07 | 0.84 |
| Turn Over Number (TON) of catalyst at the end of one fresh & two recycle runs, kg of vinyl ester/1 gm of Palladium | 21.7 | 15.2 |
| Hourly Catalytic Productivity, kg vinyl ester/gm Palladium/hr | 0.182 | 0.125 |
| Rate of formation of product kg/l-h | 0.017 | 0.012 |
| Productivity of vinyl ester, kg of vinyl ester/Liter | 0.68 | 0.48 |

Note:
The catalyst was active after recycle.

TABLE 12

Vinyl ester production reaction performance.

| | Example 43: Vinyl neodecanoate production: Fresh catalyst @ 750 ppm | Example 44: Vinyl neodecanoate production: Fresh catalyst @ 1000 ppm |
| --- | --- | --- |
| Size of pilot batch | 3.5 | 3.5 |
| Yield of NAVE-10 ester, wt % (based on weight of reaction mixture in reactor and reboiler), fresh catalyst | 80.86 | 90.90 |
| Yield of NAVE-10 ester, wt %, 1$^{st}$ recycle | 75.44 | 77 |
| Moles of carboxylic acid input | 11.63 | 11.63 |
| Amount of product formed, gm mol | 9.4 | 10.53 |
| Reaction time (Initial charge heating + Feeding mixture + Time required to achieve conversion), hr | 8 | 8 |
| VAM recycle rate to transvinylation reactor, L/h | 1.2 | 1.5 |
| Average product formation rate, gm mol of vinyl ester/1 gm of Palladium-per hr | 1.55 | 1.32 |
| Turn Over Number (TON) of catalyst at the end of one fresh & two recycle runs, kg of vinyl ester/1 gm of Palladium | 5.615 | 3.865 |
| Hourly Catalytic Productivity, kg vinyl ester/gm Palladium/hr | 0.310 | 0.262 |
| Rate of formation of product kg/l-h | 0.066 | 0.074 |
| Productivity of vinyl ester, kg of vinyl ester/Liter | 0.519 | 0.59 |

Note:
The catalyst was active after recycle.

Selectivity toward vinyl ester product formation in all of the transvinylation reactions was close to 100%. No impurities were detected in analysis by gas chromatography (GC) and gas chromatography—mass spectroscopy (GC-MS) techniques.

Product Purification and Product Specifications:

The crude product isolated in all of the pilot plant runs was 95% pure. The remaining 5% was either 2-EHA, BA, or C-10 acid with some traces of acetic acid. The crude product was subjected to fractional distillation under reduced pressure. The fractionation procedure was guided by GC analysis. Product of desired quality was isolated in all cases. The products V-2-EH and VB were stabilized by incorporating 30 ppm of MeHQ. Note that the boiling point for V-2-EH is 185.3° C., compared to the 228° C. boiling point of 2-EHA. Products having the following specifications were isolated.

TABLE 13

Analysis of Vinyl Ester Product from Pilot Plant Runs.

| | Example 41: Vinyl 2-ethyl hexanoate | Example 42: Vinyl Benzoate |
|---|---|---|
| Analytical parameter | Observed value | Observed value |
| Density | 0.86 gm/cc @ 30° C. | 1.06 gm/cc @ 30° C. |
| Acid value | 0.52 mg of KOH/gm of sample | 0.074 mg of KOH/gm of sample |
| Purity by GC | 99.68% | 99.88% |
| APHA Value | 3.3 | 15.6 |
| MS Spectra | Complies | Complies |
| NMR | Complies | Complies |

During product purification, all products were isolated with very low acid numbers. Thus, aqueous processing of product to remove acidity was avoided.

Another reaction was performed in a thermosiphon reactor. The reactor was fed VAM and C-10 acid at an initial molar ratio of about 2:1. The semi-continuous process was operated at different catalyst concentrations, viz. 500 ppm, 750 ppm and 1000 ppm Pd based on the amount of C-10 acid. The reaction system was operated in the same manner as described above. The reactor temperature reached about 98° C. and was operated for about 10 hours. At the end of this period, the reactor contents were analyzed and found to contain 57.52% vinyl neodecanoate, 22.66% vinyl acetate, 16.42% neodecanoic acid, and 3.40% acetic acid, achieving 77.79% formation of NAVE-10.

Examples 45-59

Effect of Catalyst Concentration, Temperature, and Reagent Ration on the Conversion of Carboxylic Acids The effect of catalyst (diacetato-palladium (II)-2,2'-bipyridyl) on the conversion of 2-EHA to V-2-EH or of BA to VB was studied in a batch mode. In each case, 500 gm of 2-EHA was provided to the reactor. Vinyl acetate was provided in a molar vinyl acetate:carboxylic acid ratio of 4:1. The following tables show the effect of catalyst concentration.

TABLE 14

2-EHA Conversion as a Function of Catalyst Concentration.

| | Example No. | | | |
|---|---|---|---|---|
| | 45 | 46 | 47 | 48 |
| Reaction volume, Liters | 1.83 | 1.83 | 1.83 | 1.83 |
| Pd concentration, ppm | 250 | 500 | 503 | 1000 |
| Maximum conversion of 2-EHA, wt % | 73.27 | 74.69 | 83.86 | 80.46 |
| Time required to attain 73% conversion, hr | 8 | 5.5 | 5.5 | 2.5 |
| Moles of product formed, gm mol | 2.54 | 2.534 | 2.534 | 2.56 |

TABLE 14-continued

2-EHA Conversion as a Function of Catalyst Concentration.

| | Example No. | | | |
|---|---|---|---|---|
| | 45 | 46 | 47 | 48 |
| Product formation rate, gm mol/gm Pd per hr | 1.26 | 0.92 | 0.92 | 1.013 |
| Hourly Catalytic Productivity, kg V-2-EH/gm Pd per hr | 0.215 | 0.157 | 0.157 | 0.172 |
| Product (V-2-EH) formation rate, kg/liter reactor volume-hr | 0.03 | 0.04 | 0.04 | 0.103 |

TABLE 15

BA Conversion as a Function of Catalyst Concentration.

| | Example No. | | |
|---|---|---|---|
| | 49 | 50 | 51 |
| Reaction volume, Liters | 2.01 | 2.01 | 2.06 |
| Pd concentration, ppm | 250 | 500 | 1000 |
| Maximum conversion of BA, wt % | 78.23% | 69.88% | 74.89% |
| Time required to attain max. conversion, hr | 11.5 | 8.5 | 4.42 |
| Moles of product formed, gm mol | 3.21 | 2.86 | 3.07 |
| Product formation rate, gm mol/gm Pd per hr | 2.23 | 1.35 | 1.39 |
| Hourly Catalytic Productivity, kg VB/gm Pd per hr | 0.330 | 0.200 | 0.206 |
| Product (VB) formation rate, kg/liter reactor volume-hr | 0.02 | 0.024 | 0.05 |

For C-10 acid, the effects of catalyst concentration, reaction temperature, and molar ratio of reactants were studied. In a 5 L reactor in batch mode, neodecanoic acid was reacted with vinyl acetate in the presence of a palladium-complex catalyst. Speed of agitation was 1000 rpm. In a representative example, 400 gm of C-10 acid were reacted with vinyl acetate in a molar ratio of 3 moles vinyl acetate to one mole neodecanoic acid. The reaction took place at 90° C. in the presence of 249 mg palladium catalyst to kg of neodecanoic acid. After 11 hours, 1.10 moles of vinyl neodecanoate were formed, representing a conversion of 47.26%. The rate of formation of the product was 1.00 gm mol per gm of palladium per hour, and the productivity of the reactor was 0.20 kg of product per liter of reactor volume. Representative results are provided in Tables 16-18, below. From these tests, it was determined that an acid to vinyl acetate molar ratio of about 6 achieved optimum acid conversion, and that about 750 ppm is an optimal loading value.

TABLE 16

C-10 Acid Conversion as a Function of Catalyst Concentration.

| | Example No. | | | |
|---|---|---|---|---|
| | 52 | 53 | 54 | 55 |
| Reaction volume, Liters | 1.10 | 1.10 | 1.10 | 1.10 |
| Pd concentration, ppm | 250 | 500 | 750 | 1000 |
| Maximum formation of NAVE-10, wt % | 55 | 97 | 90 | 86 |
| Time required to attain max. formation, hr | 11 | 11 | 11 | 11 |
| Moles of product formed, gm mol | 1.29 | 2.25 | 0.28 | 2.02 |
| Product formation rate, gm mol/gm Pd per hr | 1.18 | 1.03 | 0.63 | 0.63 |

TABLE 16-continued

C-10 Acid Conversion as a Function of Catalyst Concentration.

| | Example No. | | | |
|---|---|---|---|---|
| | 52 | 53 | 54 | 55 |
| Hourly Catalytic Productivity, kg NAVE-10/gm Pd per hr | 0.233 | 0.203 | 0.125 | 0.125 |
| Product (NAVE-10) formation rate, kg/liter reactor volume-hr | 0.15 | 0.26 | 0.23 | 0.23 |

Temperature: 100° C.; Molar ratio of C-10 acid:VAM 1:6.

As Table 16 shows, palladium concentrations of greater than 250 ppm are preferable to achieve satisfactory formation of vinyl neodecanoate. Further analysis has shown that at concentrations from 250 to 750 ppm, equilibrium conversion was not achieved. Therefore, concentrations of greater than 750 ppm are preferable.

TABLE 17

C-10 Acid Conversion as a Function of Temperature.

| | Example No. | | |
|---|---|---|---|
| | 56 | 55 | 57 |
| Reaction volume, Liters | 1.10 | 1.10 | 1.10 |
| Temperature, ° C. | 90 | 100 | 110 |
| Maximum formation of NAVE-10, wt % | 80 | 87 | 92 |
| Time required to attain max. formation, hr | 10 | 6 | 5 |
| Moles of product formed, gm mol | 1.84 | 2.02 | 2.14 |
| Product formation rate, gm mol/gm Pd per hr | 0.42 | 0.63 | 1.08 |
| Hourly Catalytic Productivity, kg NAVE-10/gm Pd per hr | 0.084 | 0.125 | 0.125 |
| Product (NAVE-10) formation rate, kg/liter reactor volume-hr | 0.21 | 0.23 | 0.24 |

Catalyst loading: 1000 ppm; molar ratio of C-10 acid:VAM 1:6.

As Table 17 shows, as the temperature increases, the rate of formation of vinyl neodecanoate increases.

TABLE 18

C-10 Acid Conversion as a Function of VAM to C-10 Acid Molar Ratio.

| | Example No. | | |
|---|---|---|---|
| | 58 | 55 | 59 |
| Reaction volume, Liters | 1.10 | 1.10 | 1.10 |
| Molar Ratio, VAM to C-10 acid | 3:1 | 6:1 | 9:1 |
| Maximum formation of NAVE-10, wt % | 86 | 86 | 97 |
| Time required to attain max. formation, hr | 8 | 6 | 9 |
| Moles of product formed, gm mol | 2.23 | 2.02 | 2.25 |
| Product formation rate, gm mol/gm Pd per hr | 0.49 | 0.63 | 0.63 |
| Hourly Catalytic Productivity, kg NAVE-10/gm Pd per hr | 0.097 | 0.125 | 0.125 |
| Product (NAVE-10) formation rate, kg/liter reactor volume-hr | 0.38 | 0.23 | 0.18 |

Catalyst loading: 1000 ppm; Temperature: 100° C.

Examples 60-71

Pilot Scale Study of Additional Carboxylic Acids

Example 60: Following the procedure of Examples 1-7, methacrylic acid is reacted with vinyl acetate in a molar ratio of from about 1.5 to about 4 moles of vinyl acetate per mole of carboxylic acid in the presence of a palladium catalyst in a concentration of about 1000 ppm based on the mass of carboxylic acid. The reaction mixture is maintained at about 100° C. until the desired conversion of methacrylic acid to vinyl methacrylate is achieved.

Example 61: Following the procedure of Examples 1-7, propionic acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of propionic acid to vinyl propionate is achieved.

Example 62: Following the procedure of Examples 1-7, butyric acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of butyric acid to vinyl butyrate is achieved.

Example 63: Following the procedure of Examples 1-7, valeric acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of valeric acid to vinyl valerate is achieved.

Example 64: Following the procedure of Examples 1-7, heptanoic acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of heptanoic acid to vinyl heptanoate is achieved.

Example 65-67: Following the procedure of Examples 1-7, neodecanoic acid, a mixture of neoalkanoic acids having on average ten carbon atoms, was reacted with vinyl acetate in a molar ratio of from about 1.5 to about 4 moles or 6 moles of vinyl acetate per mole of carboxylic acid in the presence of a palladium catalyst in a concentration of from about 1000 ppm based on the mass of carboxylic acid. The reaction mixture was maintained at about 100° C. until the desired conversion of neodecanoic acid to the corresponding vinyl ester, commercially known as vinyl neodecanoate (also referred to herein as neo-acid vinyl ester-10 or NAVE-10), was achieved.

The reaction mixture was then charged to a rotary evaporator, vinyl neodecanoate was allowed to distill and was separately collected. This distillate mainly contained NAVE-10 and a small amount of acetic acid and vinyl acetate, and is herein identified as crude NAVE-10. When distillation ceased, the contents were cooled and the vacuum released. The residue was preserved for recycle. This residue contained mainly neodecanoic acid, a small amount of vinyl decanoate, and the catalyst.

The process was performed using a variety of equipment to analyze the effects. These systems included: (1) a series of two continuously stirred-tank reactors (CSTRs) and a reboiler; (2) a single CSTR and a reboiler; (3) a bubble column in conjunction with a reactive distillation column; and (4) a thermosiphon reactor. Each system was equipped with columns and operated consistently with the description provided above.

The CSTRs in series were run until steady state formation of NAVE-10 was achieved. The feed flowrate of C-10 acid was varied from 4.5 ml/min to 3.5 ml/min to analyze the effect of residence time on ester formation. The reflux ratio was gradually increased to 5:1. After the reaction, the reaction mixture was cooled, weighed, and charged to a rotary evaporator for recovery of components. At equilibrium, the formation of vinyl ester was slightly higher with the lower feedrate (3.5 ml/min), achieving about 62-64% formation of NAVE-10.

A similar experiment was run with one CSTR, otherwise operated identically to the two-CSTR system. The single reactor system achieved a 58% formation of vinyl ester.

The process was also performed using a bubble column and a reactive distillation column, as discussed in more detail above. The catalyst was provided at a concentration of 1000 ppm. VAM was provided at a rate of 40 ml/min, and C-10 acid was provided at a rate of 8 ml/min. It was discovered that about 15-20% of the NAVE-10 produced was formed in the reactive distillation column, and about 65-69% was formed in the bubble column reactor. In total, about 80% formation of NAVE-10 was achieved.

Finally, the process was performed using a thermosiphon reactor with a preheater and a reboiler, consistent with the procedure discussed above. The feed rate of VAM was 52 ml/min, and the feed rate of C-10 acid was varied from 10 to 20 ml/min. The reactor was maintained at a temperature of about 95-99° C. It was discovered that catalyst life was improved due to the avoidance of localized temperature peaks at the skin of the reactor. A steady-state NAVE-10 formation of about 63% was achieved.

TABLE 19

Continuous NAVE-10 Reactive Distillation Conditions and Performance.

| | Example No. | | |
|---|---|---|---|
| | 65 | 66 | 67 |
| Apparatus Type | Thermosiphon (TSR) | BCR | 2-CSTRs |
| C-10 acid feed rate, g/h | 761 | 435 | 245 |
| Palladium conc. on C-10 acid basis, ppm | 1000 | 1000 | 1000 |
| Palladium, g/h | 0.761 | 0.435 | 0.245 |
| VAM feed rate, g/h | 3120 | 2232 | 780 |
| Mole ratio of VAM to C-10 acid as fed to reactor | 1.9 | 10 | 2 |
| Reaction temp., ° C. | 100 | 100 | 100 |
| Reactor Volume based on voidage, L | 12 | 10.5 | 3.5 + 4.5 |
| Residence time, h | 13 | 19 | 12 |
| Vinyl ester formed, g/h | 551 | 330 | 174 |
| Conversion of C-10 acid, % | 63 | 66 | 62 |
| Selectivity of C-10 acid to NAVE-10, % | 100 | 100 | 100 |
| Hourly Catalytic Productivity, kg NAVE-10/h-g Pd | 0.551 | 0.435 | 0.174 |
| Initial Turn Over Number, kg NAVE-10/g Pd (assuming steady-state operation for a duration of 5 times the residence time) | 35.8 | 41.3 | 10.44 |

Characteristics of the NAVE-10 product are presented in Table 20, below.

TABLE 20

Analysis of Vinyl Ester Product from Pilot Plant Runs.

Examples 65-67

| Analytical parameter | Observed value |
|---|---|
| Density | 0.8770 gm/cc @ 25° C. |
| Acid value | 0.158 mg of KOH/gm of sample |
| Purity by GC | 99.7% |
| APHA Value | 6.81 |

TABLE 20-continued

Analysis of Vinyl Ester Product from Pilot Plant Runs.

Examples 65-67

| MS Spectra | COMPLIES |
|---|---|
| NMR | COMPLIES |

Example 68: Following the procedure of Examples 1-7, acrylic acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of acrylic acid to vinyl acrylate is achieved.

Example 69: Following the procedure of Examples 1-7, stearic acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of stearic acid to vinyl stearate is achieved.

Example 70: Following the procedure of Examples 1-7, palmitic acid is reacted with vinyl acetate in a molar ratio of from about 1.5 to about 4 moles of vinyl acetate per mole of carboxylic acid in the presence of a palladium catalyst in a concentration of from about 1000 ppm based on the mass of carboxylic acid. The reaction mixture is maintained at about 100° C. until the desired conversion of palmitic acid to vinyl palmitate is achieved.

There is thus provided in accordance with the present invention a continuous process for selective formation of vinyl ester from its corresponding carboxylic acid. In the formation process, carboxylic acid and vinyl acetate are fed to a reactor and reacted in the presence of a homogeneous transvinylation catalyst in a reaction mixture to form a vinyl ester product and acetic acid. Acetic acid and vinyl acetate are preferably continuously removed from the reaction mixture and at least a portion of the vinyl acetate is separated from the removed acetic acid and recycled to the reaction mixture. The reaction mixture may be continuously withdrawn as a crude vinyl ester product mixture which includes residual carboxylic acid, residual vinyl acetate, residual acetic acid, and homogeneous transvinylation catalyst; and a purified vinyl ester product may be separated from the residual carboxylic acid, residual vinyl acetate, residual acetic acid, and homogeneous transvinylation catalyst.

The process according to the invention is generally characterized by conversion of carboxylic acid to vinyl ester product with a selectivity of at least 80 mole %, less than 15 weight % acetic acid in the crude product mixture, and a molar ratio of vinyl acetate:carboxylic acid maintained in the reaction mixture of from 1:1 to 10:1. These characteristics may be achieved by selection of catalyst and by controlling the reaction conditions, feed to the reaction mixture, removal of acetic acid from the reaction mixture, and the separation and recycling of vinyl acetate to the reaction mixture.

In one embodiment, the concentration of acetic acid in the crude product mixture is less than 10 weight % with a molar ratio of vinyl acetate:carboxylic acid of from 1:1 to 6:1 in the reaction mixture. In another embodiment, the concentration of acetic acid in the crude product mixture is less than 5 weight % with a vinyl acetate:carboxylic acid reactant molar ratio of from 1:1 to 9:1 or 1:1 to 4:1. In still another embodiment, the concentration of acetic acid in the crude product mixture is less than 15 weight % acetic acid with a vinyl acetate:carboxylic acid reactant molar ratio of from about 1.5:1 up to about 3:1. In yet another embodiment, the concentration of acetic acid in the crude product mixture is less than 15 weight % acetic with a vinyl acetate:carboxylic acid reactant molar ratio of more than 2:1.

The process generally comprises separating residual carboxylic acid from the crude vinyl ester product mixture and recycling the residual carboxylic acid to the reaction mixture. Typically, the process further comprises separating the homogeneous transvinylation catalyst from the crude vinyl ester product mixture and recycling the catalyst to the reaction mixture.

Generally, the separated vinyl acetate is recycled at a rate of less than about 8 kg of vinyl acetate for every kg of vinyl ester produced. Preferably, vinyl acetate is recycled at a rate of less than about 7 kg of vinyl acetate per kg of vinyl ester product. More preferably, the vinyl acetate is recycled at a rate of less than about 6 kg of vinyl acetate per kg of vinyl ester product. Typically, from about 4 kg to about 8 kg of vinyl acetate is recycled per kg of vinyl ester product. Still more preferably, from about 6 to about 7 kg of vinyl acetate is recycled per kg of vinyl ester product.

The inhibitor is generally selected from the group consisting of hydroquinone (HQ), methoxy hydroquinone (MEHQ), butylated hydroxytoluene (BHT), tert-butyl catechol (TBC), diphenylamine, phenothiazine and a hindered phenol. The carboxylic acid is generally selected from the group consisting of 2-ethylhexanoic acid, benzoic acid, methacrylic acid, neodecanoic acid, propionic acid, butyric acid, valeric acid, heptanoic acid, acrylic acid, stearic acid, and palmitic acid.

In one embodiment, more than 60 weight % of the carboxylic acid provided is converted to vinyl ester. In another embodiment, more than 65 weight % of the carboxylic acid provided is converted to vinyl ester. Preferably, more than 70 weight % of the carboxylic acid provided is converted to vinyl ester product. More preferably, more than 75 weight % of the carboxylic acid provided is converted to vinyl ester. The carboxylic acid conversion recited may likewise refer to ester conversion as defined herein.

In one aspect of the invention, the process generally provides a vinyl ester product at a selectivity of greater than 90 mole %, typically greater than 95 mole %, based on the carboxylic acid provided. In another aspect of the invention, the process provides a vinyl ester product at a selectivity of greater than 99 mole % based on the carboxylic acid provided.

In accordance with the invention, the reaction is carried out under reactive distillation conditions wherein vinyl acetate and by-product acetic acid are removed as distillate from the reaction mixture. The temperature of the reaction is generally maintained at from about 80° C. up to about 120° C. Preferably, the temperature is from about 90° C. to about 110° C. More preferably, the temperature is from about 90° C. to about 105° C.

Typically, unreacted vinyl acetate and acetic acid are continuously removed from the reaction mixture in a vinyl acetate:acetic acid molar ratio of from about 5:1 to about 25:1, and in some cases, in a vinyl acetate:acetic acid molar ratio of from about 6:1 to about 10:1.

Preferably, the process is characterized by an Hourly Catalytic Productivity of at least 0.1 kg vinyl ester product per gm catalyst metal per hour. More preferably, the process is characterized by an Hourly Catalytic Productivity of at least 0.3 or 0.5 kg vinyl ester product per gm catalyst metal per hour. Still more preferably, the Hourly Catalytic Productivity is at least 0.7 kg vinyl ester product per gm catalyst metal per hour.

In an aspect of the invention, the reaction may carried out in a bubble column. The process is generally operated at a residence time for reactant carboxylic acid of from about 15 minutes or about 4 or 5 hours to about 20 hours. The residence time is preferably from about 10 to about 20 hours and more preferably from about 5 to about 15 hours.

Preferably, the homogeneous transvinylation catalyst comprises a platinum group metal.

A particularly useful commercial embodiment is a continuous process for selective formation of vinyl ester by reactive distillation from its corresponding carboxylic acid. Carboxylic acid and vinyl acetate are fed to a reactor and reacted in the presence of a palladium acetate—bidentate ligand catalyst complex in a reaction mixture to form a vinyl ester product and acetic acid while the acetic acid and vinyl acetate are continuously removed from the reaction mixture. At least a portion of the removed vinyl acetate is separated from the removed acetic acid and recycled to the reaction mixture. The reaction mixture is withdrawn as a crude vinyl ester product mixture which includes residual carboxylic acid, residual vinyl acetate, residual acetic acid, and palladium acetate—bidentate ligand catalyst complex. Residual reactants including carboxylic acid and vinyl acetate; residual acetic acid byproduct; and palladium acetate—bidentate ligand catalyst complex are separated from the crude vinyl ester product mixture to form a purified vinyl ester product.

The process is characterized by a vinyl ester product selectivity of at least 80 mole % and an acetic acid concentration in the crude product mixture of less than 15 weight % as well as a vinyl acetate:carboxylic acid molar ratio of from 1:1 to 6:1 maintained in the reaction mixture. These characteristics are achieved by catalyst selection and control of the reaction conditions, feed to the reaction mixture, removal of acetic acid from the reaction mixture, and the separation and recycling of vinyl acetate to the reaction mixture.

The catalyst concentration provided is typically from about 50 or 150 parts palladium per million to about 2325 or about 3000 parts palladium per million parts of carboxylic acid provided. Preferably, the catalyst concentration provided is from about 500 to about 1500 parts palladium per million parts of carboxylic acid.

Generally, the process is characterized by an initial turnover number of more than about 10 kg of vinyl ester per gram of palladium contained in the palladium acetate—bidentate ligand catalyst complex utilized. In one embodiment, the initial turnover number is more than about 20 kg of vinyl ester per gram of palladium. In another embodiment, the turnover number is more than 30 kg of vinyl ester per gram of palladium. In a further embodiment, the initial turnover number is more than 40 kg of vinyl ester per gram of palladium.

Typically, the process is operated in a continuous mode, wherein vinyl ester product is continuously withdrawn from the reaction mixture.

The palladium acetate—bidentate ligand catalyst complex is characterized by a mole ratio of palladium acetate to bidentate ligand of from about 1:1 to about 1:1.5 or about 1:2. The bidentate ligand is selected from the group consisting of 2,2'-bipyridyl, 1,10-phenanthroline, N,N,N',N'-tetramethylethylenediamine and P,P,P',P'-tetraphenyl-1,2-diphosphinoethane.

In an aspect of the invention, the carboxylic acid may be purified prior to reaction. A purified carboxylic acid is generally evidenced by a bromine value of less than 20 mmoles of $Br_2/g$, a peroxide value of less than 200 ppm, or a permanganate time of at least 30 minutes.

One embodiment provides for a continuous process for selective formation of vinyl ester from neodecanoic acid. Raw neodecanoic acid is purified and then reacted with vinyl acetate in the presence of a homogeneous transvinylation catalyst to form a vinyl neodecanoate product and acetic acid. Acetic acid and vinyl acetate are preferably continuously removed from the reaction mixture and at least a portion of the vinyl acetate is separated from the acetic acid and recycled to the reaction mixture. The reaction mixture may be continuously withdrawn and vinyl neodecanoate product may be separated from residual neodecanoic acid, residual vinyl acetate, residual acetic acid, and homogeneous transvinylation catalyst. The process is generally characterized by a conversion of neodecanoic acid to vinyl ester product with a selectivity of at least 80 mole %, and a crude product mixture containing less than 15 weight % acetic acid. A molar ratio of vinyl acetate:carboxylic acid of from 1:1 to 9:1 is generally maintained in the reaction mixture.

More specifically, one embodiment provides for a process for purifying a carboxylic acid. In this embodiment, a raw carboxylic acid is purified using a method selected from the group consisting of flash distillation; fractionation; extraction; hydrogenation; and combinations thereof. The purification process is characterized by a purified carboxylic acid containing less than 1 weight % impurities selected from the group consisting of compounds having alcohol functional groups; compounds having ester functional groups; compounds having alkene functional groups; compounds having peroxide functional groups; sulfur; and other electropositive metals.

The purification method may include at least hydrogenation. The hydrogenation may be performed with a palladium catalyst supported on carbon or another suitable catalyst that remains active for several cycles of hydrogenation; such as for at least about 25 cycles and up to about 50 cycles of hydrogenation or for at least 50 cycles of hydrogenation; in any case, the catalyst preferably remains active for more than about 30 cycles of hydrogenation. The conditions may include a temperature in the range of about 50-150° C. and a pressure in the range of about 5-25 kg/cm$^2$.

Alternatively, the purification method may include at least multistage extraction with water. In the extraction step, the carboxylic acid is agitated with water for from about ½ hour to about 6 hours, such as for about 2 hours. The carboxylic acid is subsequently recovered by phase separation, for which the carboxylic acid-water mixture is allowed to settle for from about 10 minutes to about 2 hours.

In another embodiment, a process is provided for selective formation of a vinyl ester from a corresponding carboxylic acid of suitable purity to ameliorate catalyst poisoning. In this process, a carboxylic acid, vinyl acetate, and a homogeneous transvinylation platinum-group metal catalyst are provided to a reaction mixture. The carboxylic acid is generally characterized by at least one of the following parameters: a bromine value of less than 20 mmoles of Br$_2$/g; a peroxide value of less than 200 ppm; or permanganate time of at least 30 minutes. The carboxylic acid and vinyl acetate are reacted in the presence of the homogeneous transvinylation catalyst in the reaction mixture to form a vinyl ester product and acetic acid. Acetic acid and vinyl acetate are removed from the reaction mixture and at least a portion of the vinyl acetate is separated and recycled to the reaction mixture. Residual carboxylic acid and vinyl acetate reactants, acetic acid, and catalyst are separated from the crude vinyl ester product mixture to form a purified vinyl ester product. The process is characterized by a selectivity of at least 80 mole %, less than 15 weight % acetic acid in the crude product mixture, and a molar ratio of vinyl acetate:carboxylic acid of from 1:1 to 9:1 maintained in the reaction mixture. In one aspect of the invention, the carboxylic acid is neodecanoic acid.

Preferably, the carboxylic acid is characterized by at least one of: a bromine value of 18 mmoles of Br$_2$/g or less, a peroxide value of less than 100 ppm, or a permanganate time of more than 60 minutes. More preferably, the carboxylic acid is characterized by at least one of: a bromine value of less than 10 mmoles of Br$_2$/g, a peroxide value of less than 20 ppm, or a permanganate time of more than 120 minutes.

While the invention has been described in detail, modifications within the spirit and scope of the invention will be readily apparent to those of skill in the art. In view of the foregoing discussion, relevant knowledge in the art and references including co-pending applications discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A continuous process for selective formation of a vinyl ester from its corresponding carboxylic acid, the process comprising:
   (a) providing a carboxylic acid, vinyl acetate, and a homogeneous transvinylation catalyst comprising palladium to a reaction mixture;
   (b) reacting the carboxylic acid and vinyl acetate in the presence of the homogeneous transvinylation catalyst comprising palladium in the reaction mixture to form a vinyl ester product and acetic acid;
   (c) continuously removing acetic acid and vinyl acetate from the reaction mixture wherein vinyl acetate and acetic acid are continuously removed from the reaction mixture and the vinyl acetate:acetic acid molar ratio is from about 5:1 to about 25:1;
   (d) separating at least a portion of the removed vinyl acetate from the removed acetic acid and recycling the separated vinyl acetate to the reaction mixture;
   (e) continuously withdrawing reaction mixture as a crude vinyl ester product mixture which includes residual carboxylic acid, residual vinyl acetate, residual acetic acid, and homogeneous transvinylation catalyst; and
   (f) separating residual carboxylic acid, residual vinyl acetate, residual acetic acid, and homogeneous transvinylation catalyst from the crude vinyl ester product mixture to form a purified vinyl ester product;
wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate:carboxylic acid of from more than 2:1 to 10:1 maintained in the reaction mixture.

2. The process according to claim 1, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 10 weight % acetic acid in the crude product mixture as well as a molar ratio of vinyl acetate: carboxylic acid of from more than 2:1 to 6:1 maintained in the reaction mixture.

3. The process according to claim 1, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 5 weight % acetic acid in the crude product mixture as well as a molar ratio of vinyl acetate: carboxylic acid of from more than 2:1 to 4:1 maintained in the reaction mixture.

4. The process according to claim 1, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate: carboxylic acid of from more than 2:1 up to about 3:1 maintained in the reaction mixture.

5. The process according to claim 4, wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture.

6. The process according to claim 1, wherein the process further comprises separating residual carboxylic acid from the crude vinyl ester product mixture and recycling the residual carboxylic acid to the reaction mixture.

7. The process according to claim 1, wherein the process further comprises separating the homogeneous transvinylation catalyst from the crude vinyl ester product mixture and recycling the catalyst to the reaction mixture.

8. The process according to claim 1, wherein the separated vinyl acetate is recycled at a rate of less than about 8 kg of vinyl acetate for every kg of vinyl ester produced.

9. The process according to claim 1, wherein more than 60 weight % of the carboxylic acid provided is converted to vinyl ester.

10. The process according to claim 1, wherein the carboxylic acid is selected from the group consisting of 2-ethylhexanoic acid, benzoic acid, neodecanoic acid, propionic acid, butyric acid, valeric acid, heptanoic acid, acrylic acid, methacrylic acid, stearic acid, and palmitic acid.

11. The process according to claim 1, wherein the temperature of the reaction (b) is maintained at from about 80° C. up to about 120° C.

12. The process according to claim 1, wherein unreacted vinyl acetate and acetic acid are continuously removed from the reaction mixture in a vinyl acetate:acetic acid molar ratio of from about 6:1 to about 10:1.

13. A continuous process for selective formation of vinyl ester by reactive distillation from its corresponding carboxylic acid, the process comprising:
  (a) providing carboxylic acid, vinyl acetate, and a palladium acetate-bidentate ligand catalyst complex to a reaction mixture;
  (b) reacting the carboxylic acid and vinyl acetate in the presence of the palladium acetate—bidentate ligand catalyst complex in the reaction mixture to form a vinyl ester product and acetic acid;
  (c) continuously removing acetic acid and vinyl acetate from the reaction mixture in a vinyl acetate:acetic acid molar ratio of from about 6:1 to about 10:1;
  (d) separating at least a portion of the removed vinyl acetate from the removed acetic acid and recycling the separated vinyl acetate to the reaction mixture;
  (e) withdrawing reaction mixture as a crude vinyl ester product mixture which includes residual carboxylic acid, residual vinyl acetate, residual acetic acid, and palladium acetate—bidentate ligand catalyst complex; and
  (f) separating residual carboxylic acid, residual vinyl acetate, residual acetic acid, and palladium acetate—bidentate ligand catalyst complex from the crude vinyl ester product mixture to form a purified vinyl ester product;
wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate:carboxylic acid of from more than 2:1 to 6:1 maintained in the reaction mixture.

14. The process according to claim 13, wherein the catalyst concentration provided is from about 50 parts palladium per million parts of carboxylic acid provided to about 3,000 parts palladium per million parts of carboxylic acid provided.

15. A continuous process for selective formation of vinyl ester from neodecanoic acid, the process comprising:
  (a) purifying raw neodecanoic acid;
  (b) providing the neodecanoic acid, vinyl acetate, and a homogeneous transvinylation catalyst comprising palladium to a reaction mixture;
  (c) reacting the neodecanoic acid and vinyl acetate in the presence of the homogeneous transvinylation catalyst comprising palladium in the reaction mixture to form a vinyl ester product and acetic acid;
  (d) continuously removing acetic acid and vinyl acetate from the reaction mixture in a vinyl acetate:acetic acid molar ratio of from about 5:1 to about 25:1;
  (e) separating at least a portion of the removed vinyl acetate from the removed acetic acid and recycling the separated vinyl acetate to the reaction mixture;
  (f) continuously withdrawing reaction mixture as a crude vinyl ester product mixture which includes residual carboxylic acid, residual vinyl acetate, residual acetic acid, and homogeneous transvinylation catalyst; and
  (g) separating residual carboxylic acid, residual vinyl acetate, residual acetic acid, and homogeneous transvinylation catalyst from the crude vinyl ester product mixture to form a purified vinyl ester product;
wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate:carboxylic acid of from more than 2:1 to 9:1 maintained in the reaction mixture.

16. A process for selective formation of a vinyl ester from its corresponding carboxylic acid, the process comprising:
  (a) providing a carboxylic acid, vinyl acetate, and a homogeneous transvinylation platinum-group metal catalyst to a reaction mixture;

wherein the carboxylic acid is of suitable purity to ameliorate catalyst poisoning, the carboxylic acid being characterized by at least one of:
  (i) a bromine value of less than 20 mmoles of $Br_2/g$;
  (ii) a peroxide value of less than 200 ppm; or
  (iii) permanganate time of at least 30 minutes;
(b) reacting the carboxylic acid and vinyl acetate in the presence of the homogeneous transvinylation catalyst in the reaction mixture to form a vinyl ester product and acetic acid;
(c) removing acetic acid and vinyl acetate from the reaction mixture;
(d) separating at least a portion of the removed vinyl acetate from the removed acetic acid and recycling the separated vinyl acetate to the reaction mixture; and
(e) separating residual carboxylic acid, residual vinyl acetate, residual acetic acid, and homogeneous transvinylation catalyst from the crude vinyl ester product mixture to form a purified vinyl ester product;
wherein the reaction conditions, feed to the reaction mixture, removal of acetic acid from the reaction mixture, and the separation and recycling of vinyl acetate to the reaction mixture are controlled and the catalyst is selected such that carboxylic acid is converted to vinyl ester product with a selectivity of at least 80 mole %, and there is less than 15 weight % acetic acid in the crude product mixture as well as a molar ratio of vinyl acetate:carboxylic acid of from 1:1 to 9:1 maintained in the reaction mixture.

17. The process according to claim 16, wherein the carboxylic acid is neodecanoic acid.

18. The process according to claim 16, wherein the carboxylic acid is 2-ethylhexanoic acid.

19. The process according to claim 16, wherein the platinum group metal is palladium.

* * * * *